(12) United States Patent
Henderson et al.

(10) Patent No.: US 10,307,165 B2
(45) Date of Patent: Jun. 4, 2019

(54) APPARATUS AND METHOD FOR RADIALLY BUNCHING A BODILY LUMEN

(71) Applicant: Ethicon Endo-Surgery, LLC, Guaynabo, PR (US)

(72) Inventors: Cortney E. Henderson, Loveland, OH (US); Tamara S. Vetro Widenhouse, Clarksville, OH (US); Charles J. Scheib, Loveland, OH (US)

(73) Assignee: Ethicon LLC, Guaynabo, PR (US)

( * ) Notice: Subject to any disclaimer, the term of this patent is extended or adjusted under 35 U.S.C. 154(b) by 378 days.

(21) Appl. No.: 14/864,269

(22) Filed: Sep. 24, 2015

(65) Prior Publication Data
US 2017/0086825 A1     Mar. 30, 2017

(51) Int. Cl.
*A61B 17/12*     (2006.01)
*A61B 17/072*     (2006.01)
(Continued)

(52) U.S. Cl.
CPC ........ *A61B 17/12* (2013.01); *A61B 17/06166* (2013.01); *A61B 17/072* (2013.01);
(Continued)

(58) Field of Classification Search
CPC ............ A61B 17/06166; A61B 17/072; A61B 17/1114; A61B 17/1155; A61B 17/12009;
(Continued)

(56) References Cited

U.S. PATENT DOCUMENTS 3,086,265 A * 4/1963 Orenick ............. B65D 63/1072
174/40 CC
3,570,497 A * 3/1971 Lemole .................. A61B 17/04
24/16 PB
(Continued)

FOREIGN PATENT DOCUMENTS

EP      0 641 546 A1    3/1995
EP      1 820 454 A2    8/2007
(Continued)

OTHER PUBLICATIONS

European Search Report, Partial, dated Jan. 5, 2017 for Application No. EP 16190332.3, 7 pgs.
(Continued)

*Primary Examiner* — Jing Ou
(74) *Attorney, Agent, or Firm* — Frost Brown Todd LLC

(57) ABSTRACT

An apparatus includes a locking portion, a flexible pulling portion, a flexible body, and a plurality of barb features extending laterally from the body. The locking portion is configured to receive the pulling portion. The pulling portion is configured to engage and translate relative to the locking portion after the locking portion has received the pulling portion. The flexible body extends from the locking portion to the pulling portion. The flexible body is configured to form a loop when the pulling portion engages the locking portion. The loop is configured to decrease in size in response to pulling of the pulling portion relative to the locking portion. The barb features are configured to engage (Continued)

a tubular region of tissue and thereby form pleats in the tubular region of tissue.

17 Claims, 22 Drawing Sheets

(51) Int. Cl.
| | |
|---|---|
| A61B 17/08 | (2006.01) |
| A61B 17/06 | (2006.01) |
| A61B 17/11 | (2006.01) |
| A61B 17/115 | (2006.01) |
| B24D 3/00 | (2006.01) |
| D04H 1/435 | (2012.01) |
| D04H 1/60 | (2006.01) |
| D04H 3/011 | (2012.01) |
| D04H 3/12 | (2006.01) |
| A61B 17/00 | (2006.01) |
| A61B 17/04 | (2006.01) |

(52) U.S. Cl.
CPC ....... *A61B 17/1114* (2013.01); *A61B 17/1155* (2013.01); *A61B 17/12009* (2013.01); *B24D 3/002* (2013.01); *D04H 1/435* (2013.01); *D04H 1/60* (2013.01); *D04H 3/011* (2013.01); *D04H 3/12* (2013.01); *A61B 17/0401* (2013.01); *A61B 2017/00398* (2013.01); *A61B 2017/00734* (2013.01); *A61B 2017/00818* (2013.01); *A61B 2017/0464* (2013.01); *A61B 2017/06176* (2013.01); *A61B 2017/07257* (2013.01); *A61B 2017/1142* (2013.01); *A61B 2017/1157* (2013.01)

(58) Field of Classification Search
CPC ...... A61B 17/0401; A61B 2017/00398; A61B 2017/00734; A61B 2017/00818; A61B 2017/0464; A61B 2017/06176; A61B 2017/07257; A61B 2017/1142; A61B 2017/1157; A61B 2017/00579; A61B 2017/0412; A61B 2017/0427; A61B 17/12
See application file for complete search history.

(56) References Cited

U.S. PATENT DOCUMENTS

| | | | |
|---|---|---|---|
| 4,191,334 A * | 3/1980 | Bulanda | F16L 3/233 24/16 PB |
| 4,473,524 A * | 9/1984 | Paradis | B29C 45/0055 24/16 PB |
| 4,805,823 A | 2/1989 | Rothfuss | |
| 4,950,285 A * | 8/1990 | Wilk | A61B 17/06 24/16 PB |
| 5,205,459 A | 4/1993 | Brinkerhoff et al. | |
| 5,269,803 A * | 12/1993 | Geary | A61B 17/1322 606/201 |
| 5,271,544 A | 12/1993 | Fox et al. | |
| 5,275,322 A | 1/1994 | Wolf et al. | |
| 5,285,945 A | 2/1994 | Brinkerhoff et al. | |
| 5,292,053 A | 3/1994 | Smith et al. | |
| 5,333,773 A | 8/1994 | Main et al. | |
| 5,350,104 A | 9/1994 | Main et al. | |
| 5,415,334 A | 5/1995 | Williamson et al. | |
| 5,465,895 A | 11/1995 | Knodel et al. | |
| 5,533,661 A | 7/1996 | Main et al. | |
| 5,597,107 A | 1/1997 | Knodel et al. | |
| 5,632,432 A | 5/1997 | Schulze et al. | |
| 5,673,840 A | 10/1997 | Schulze et al. | |
| 5,704,534 A | 1/1998 | Huitema et al. | |
| 5,741,274 A * | 4/1998 | Lenker | A61B 17/115 606/142 |
| 5,814,055 A | 9/1998 | Knodel et al. | |
| 5,836,053 A * | 11/1998 | Davignon | F16L 3/233 24/16 PB |
| 6,258,107 B1 | 7/2001 | Balazs et al. | |
| 6,978,921 B2 | 12/2005 | Shelton, IV et al. | |
| 7,000,818 B2 | 2/2006 | Shelton, IV et al. | |
| 7,143,923 B2 | 12/2006 | Shelton, IV et al. | |
| 7,303,108 B2 | 12/2007 | Shelton, IV | |
| 7,367,485 B2 | 5/2008 | Shelton, IV et al. | |
| 7,380,695 B2 | 6/2008 | Doll et al. | |
| 7,380,696 B2 | 6/2008 | Shelton, IV et al. | |
| 7,404,508 B2 | 7/2008 | Smith et al. | |
| 7,434,715 B2 | 10/2008 | Shelton, IV et al. | |
| 7,721,930 B2 | 5/2010 | McKenna et al. | |
| 7,794,475 B2 | 9/2010 | Hess et al. | |
| 8,211,126 B2 | 7/2012 | Yeh et al. | |
| 8,408,439 B2 | 4/2013 | Huang et al. | |
| 8,453,914 B2 | 6/2013 | Laurent et al. | |
| 8,800,842 B2 | 8/2014 | Menzel | |
| 8,910,847 B2 | 12/2014 | Nalagatla et al. | |
| 9,138,225 B2 | 9/2015 | Huang et al. | |
| 9,161,803 B2 | 10/2015 | Yates et al. | |
| 9,289,207 B2 | 3/2016 | Shelton, IV | |
| 9,463,022 B2 | 10/2016 | Swayze et al. | |
| 9,498,222 B2 | 11/2016 | Scheib et al. | |
| 9,532,783 B2 | 1/2017 | Swayze et al. | |
| 2001/0044637 A1 * | 11/2001 | Jacobs | A61B 17/064 606/221 |
| 2004/0068292 A1 * | 4/2004 | Koseki | A61B 17/06 606/224 |
| 2006/0123603 A1 * | 6/2006 | Hewes | B65D 63/1072 24/16 PB |
| 2008/0262534 A1 * | 10/2008 | O'Neil | A61B 17/1322 606/203 |
| 2009/0149876 A1 * | 6/2009 | Patel | A61B 17/12009 606/151 |
| 2009/0270923 A1 * | 10/2009 | Tormala | A61B 17/823 606/263 |
| 2010/0234862 A1 * | 9/2010 | Patel | A61B 17/12009 606/151 |
| 2010/0292793 A1 * | 11/2010 | Hoglund | A61B 17/12009 623/13.14 |
| 2010/0298828 A1 * | 11/2010 | Chico Roca | A61B 17/688 606/74 |
| 2011/0152900 A1 * | 6/2011 | Regadas | A61B 17/1114 606/153 |
| 2011/0313431 A1 * | 12/2011 | Shimko | A61B 17/0401 606/139 |
| 2012/0053617 A1 * | 3/2012 | Benz | A61B 17/1325 606/203 |
| 2014/0151429 A1 | 6/2014 | Scheib et al. | |
| 2014/0151430 A1 | 6/2014 | Scheib et al. | |
| 2014/0158747 A1 | 6/2014 | Measamer et al. | |
| 2014/0166728 A1 | 6/2014 | Swayze et al. | |
| 2014/0236227 A1 * | 8/2014 | Nash | A61B 17/085 606/216 |
| 2015/0083772 A1 | 3/2015 | Miller et al. | |
| 2015/0083773 A1 | 3/2015 | Measamer et al. | |
| 2015/0083774 A1 | 3/2015 | Measamer et al. | |
| 2015/0083775 A1 | 3/2015 | Leimbach et al. | |
| 2015/0142008 A1 * | 5/2015 | Hsiao | A61B 17/122 606/120 |
| 2015/0313656 A1 * | 11/2015 | Hulliger | A61B 17/823 606/74 |
| 2016/0374666 A1 | 12/2016 | DiNardo et al. | |
| 2016/0374670 A1 | 12/2016 | Fox et al. | |

FOREIGN PATENT DOCUMENTS

| | | |
|---|---|---|
| WO | WO 2005/115254 A2 | 12/2005 |
| WO | WO 2013/185484 A1 | 12/2013 |

OTHER PUBLICATIONS

European Search Report and Written Opinion dated Apr. 7, 2017 for Application No. EP 16190332.3, 11 pgs.

(56) References Cited

OTHER PUBLICATIONS

International Search Report and Written Opinion dated Apr. 7, 2017 for Application No. PCT/US2016/052768, 20 pgs.

* cited by examiner

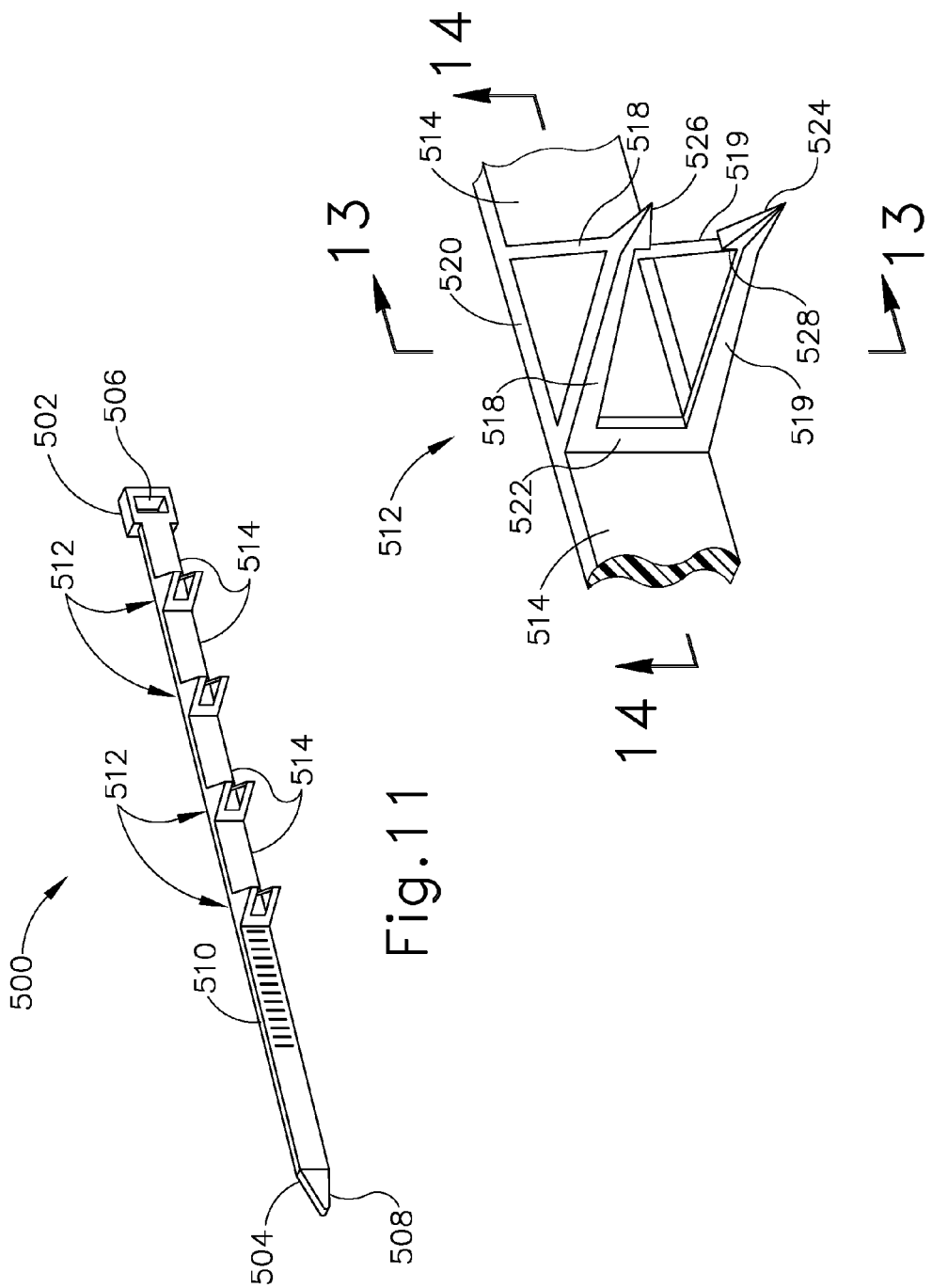

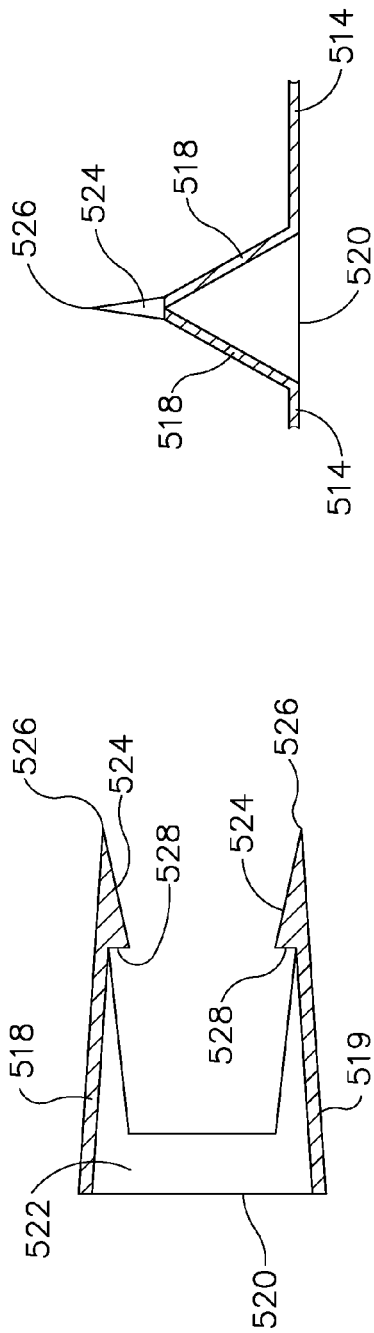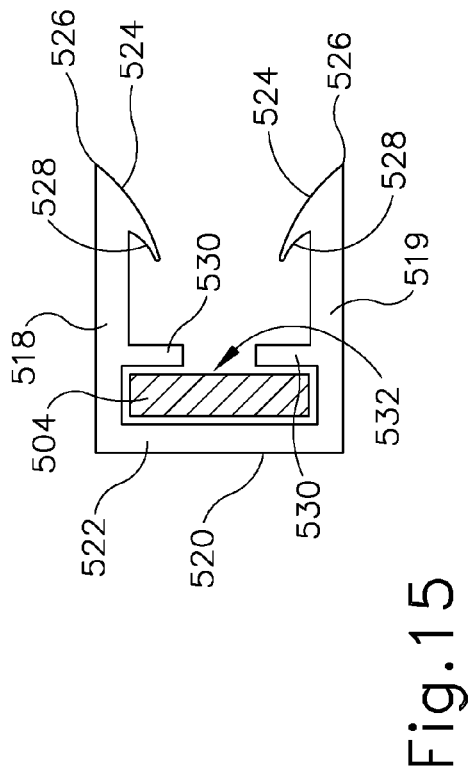
Fig.13   Fig.14   Fig.15

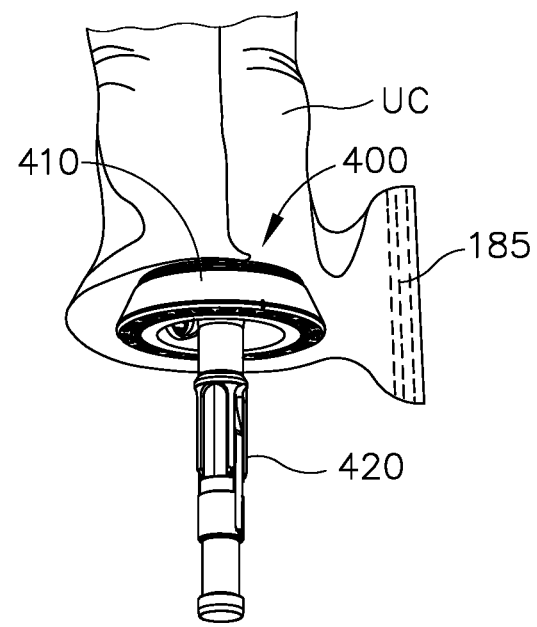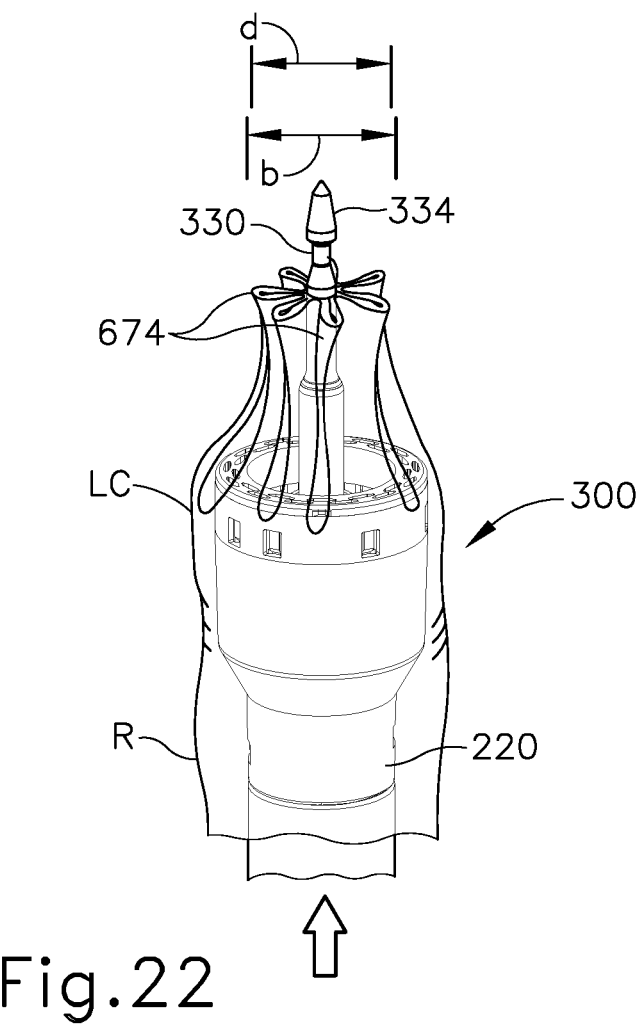
Fig.22

APPARATUS AND METHOD FOR RADIALLY BUNCHING A BODILY LUMEN

BACKGROUND

In some surgical procedures (e.g., colorectal, bariatric, thoracic, etc.), portions of a patient's digestive tract (e.g., the gastrointestinal tract and/or esophagus, etc.) may be cut and removed to eliminate undesirable tissue or for other reasons. Once the tissue is removed, the remaining portions of the digestive tract may be coupled together in an end-to-end anastomosis. The end-to-end anastomosis may provide a substantially unobstructed flow path from one portion of the digestive tract to the other portion of the digestive tract, without also providing any kind of leaking at the site of the anastomosis.

One example of an instrument that may be used to provide an end-to-end anastomosis is a circular stapler. Some such staplers are operable to clamp down on layers of tissue, cut through the clamped layers of tissue, and drive staples through the clamped layers of tissue to substantially seal the layers of tissue together near the severed ends of the tissue layers, thereby joining the two severed ends of the anatomical lumen together. The circular stapler may be configured to sever the tissue and seal the tissue substantially simultaneously. For instance, the circular stapler may sever excess tissue that is interior to an annular array of staples at an anastomosis, to provide a substantially smooth transition between the anatomical lumen sections that are joined at the anastomosis. Circular staplers may be used in open procedures or in endoscopic procedures. In some instances, a portion of the circular stapler is inserted through a patient's naturally occurring orifice.

Examples of circular staplers are described in U.S. Pat. No. 5,205,459, entitled "Surgical Anastomosis Stapling Instrument," issued Apr. 27, 1993; U.S. Pat. No. 5,271,544, entitled "Surgical Anastomosis Stapling Instrument," issued Dec. 21, 1993; U.S. Pat. No. 5,275,322, entitled "Surgical Anastomosis Stapling Instrument," issued Jan. 4, 1994; U.S. Pat. No. 5,285,945, entitled "Surgical Anastomosis Stapling Instrument," issued Feb. 15, 1994; U.S. Pat. No. 5,292,053, entitled "Surgical Anastomosis Stapling Instrument," issued Mar. 8, 1994; U.S. Pat. No. 5,333,773, entitled "Surgical Anastomosis Stapling Instrument," issued Aug. 2, 1994; U.S. Pat. No. 5,350,104, entitled "Surgical Anastomosis Stapling Instrument," issued Sep. 27, 1994; and U.S. Pat. No. 5,533,661, entitled "Surgical Anastomosis Stapling Instrument," issued Jul. 9, 1996; and U.S. Pat. No. 8,910,847, entitled "Low Cost Anvil Assembly for a Circular Stapler," issued Dec. 16, 2014. The disclosure of each of the above-cited U.S. patents is incorporated by reference herein.

Some circular staplers may include a motorized actuation mechanism. Examples of circular staplers with motorized actuation mechanisms are described in U.S. Pub. No. 2015/0083772, now abandoned, entitled "Surgical Stapler with Rotary Cam Drive and Return," published Mar. 26, 2015; U.S. Pub. No. 2015/0083773, entitled "Surgical Stapling Instrument with Drive Assembly Having Toggle Features," published Mar. 26, 2015, issued as U.S. Pat. No. 9,936,949 on Apr. 10, 2018; U.S. Pub. No. 2015/0083774, entitled "Control Features for Motorized Surgical Stapling Instrument," published Mar. 26, 2015, issued as U.S. Pat. No. 9,907,552 on Mar. 6, 2018; and U.S. Pub. No. 2015/0083775, entitled "Surgical Stapler with Rotary Cam Drive," published Mar. 26, 2015, issued as U.S. Pat. No. 9,713,469 on Jul. 25, 2017. The disclosure of each of the above-cited U.S. patent Publications is incorporated by reference herein.

While various kinds of surgical stapling instruments and associated components have been made and used, it is believed that no one prior to the inventor(s) has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 11 depicts a perspective view of an exemplary barbed cinching member;

FIG. 12 depicts a perspective view of an exemplary barbed feature of the cinching member of FIG. 11;

FIG. 13 depicts a cross-sectional view of the barbed feature of FIG. 12, taken along line 13-13 of FIG. 12;

FIG. 14 depicts a cross-sectional view of the barbed feature of FIG. 12, taken along line 14-14 of FIG. 12;

FIG. 15 depicts an end view of an alternative barbed feature that may be incorporated into the cinching member of FIG. 11;

FIG. 22 depicts a perspective view of the suture and staples of FIG. 21 attached to the colon, with the stapling head assembly of FIG. 4 positioned in the lower portion of the colon below the cinched region of the colon, with the anvil of FIG. 3 positioned in an upper portion of the colon, with the upper and lower portions of the colon separated from each other.

Figure 1:
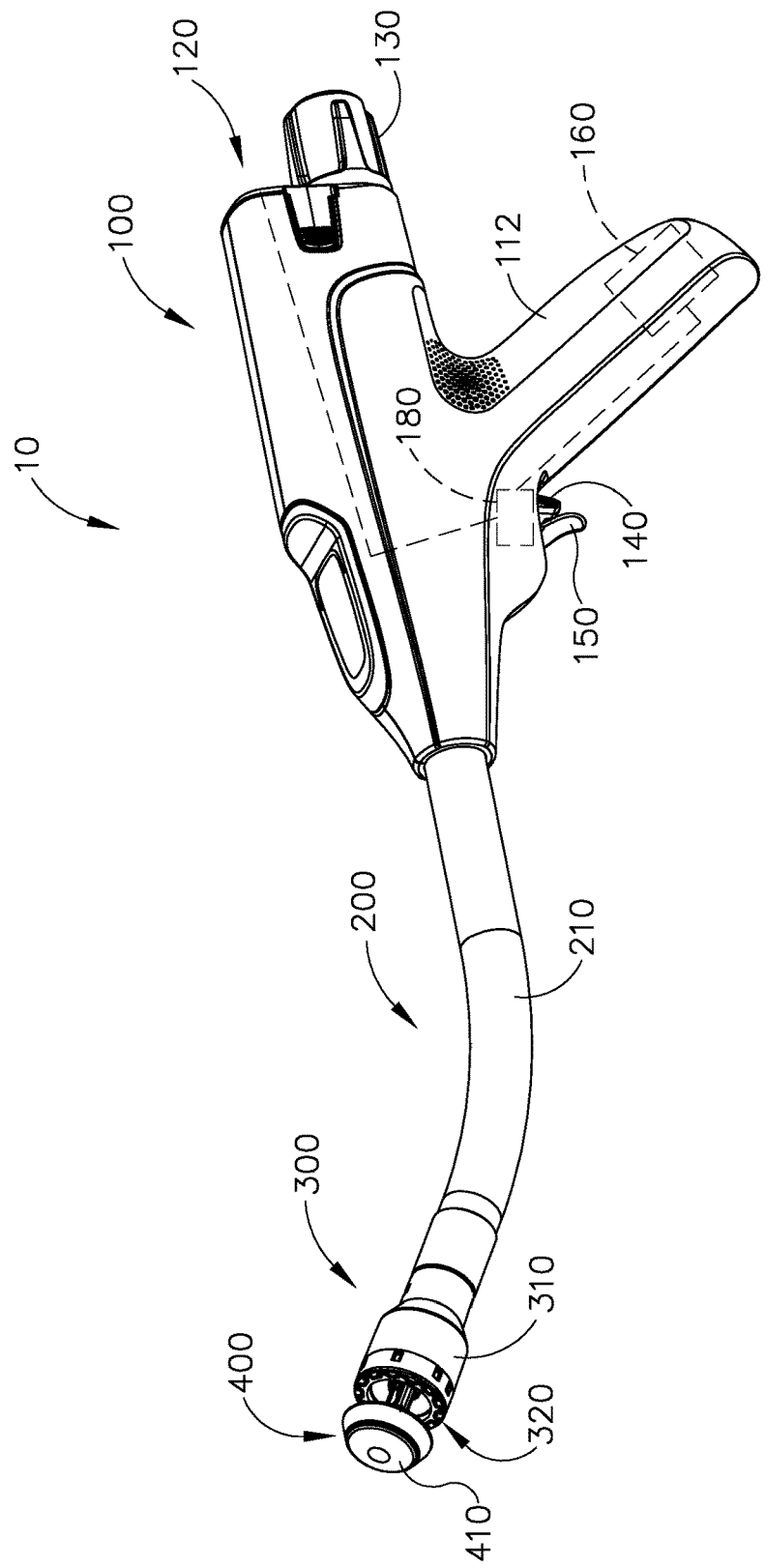
FIG. 1 depicts a perspective view of an exemplary circular stapler.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

I. Overview of Exemplary Circular Stapling Surgical Instrument

Figure 2:
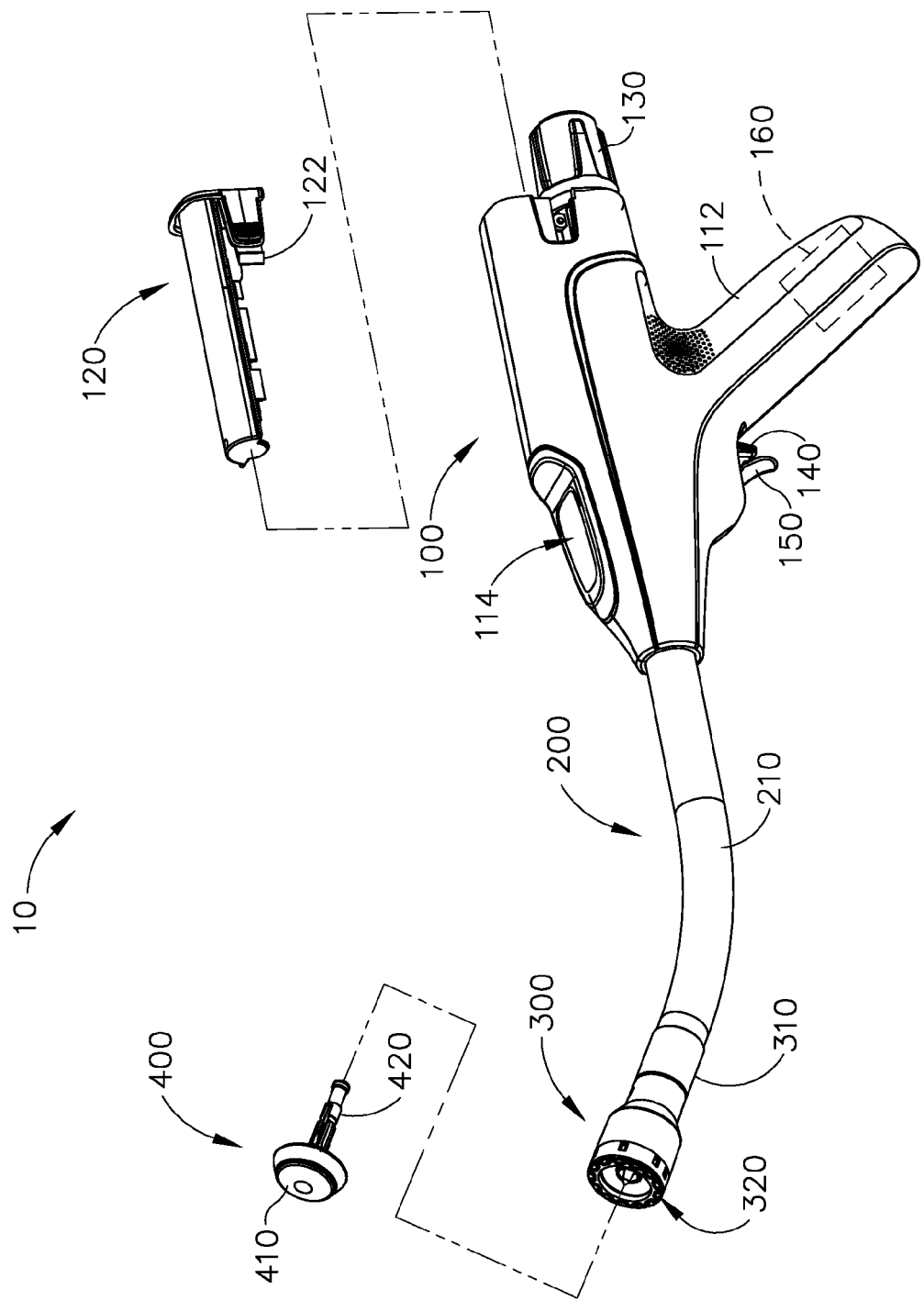
FIG. 2 depicts a perspective view of the circular stapler of FIG. 1, with a battery pack removed from a handle assembly and an anvil removed from a stapling head assembly.

FIGS. 1-2 depict an exemplary surgical circular stapling instrument (10) that may be used to provide an end-to-end anastomosis between two sections of an anatomical lumen such as a portion of a patient's digestive tract. Instrument (10) of this example comprises a handle assembly (100), a shaft assembly (200), a stapling head assembly (300), an anvil (400), and a removable battery pack (120). Each of these components will be described in greater detail below. It should be understood that, in addition to or in lieu of the following, instrument (10) may be further constructed and operable in accordance with at least some of the teachings of U.S. patent application Ser. No. 14/751,506, entitled "Anvil Stabilization Features for Surgical Stapler," filed Jun. 26, 2015, published as U.S. Pub. No. 2016/0374670 on Dec. 29, 2016; U.S. Pat. Nos. 5,205,459; 5,271,544; 5,275,322; 5,285,945; 5,292,053; 5,333,773; 5,350,104; 5,533,661; and/or 8,910,847, the disclosures of which are incorporated by reference herein. Still other suitable configurations will be apparent to one of ordinary skill in the art in view of the teachings herein.

A. Exemplary Tissue Engagement Features of Circular Stapling Instrument

Figure 3:
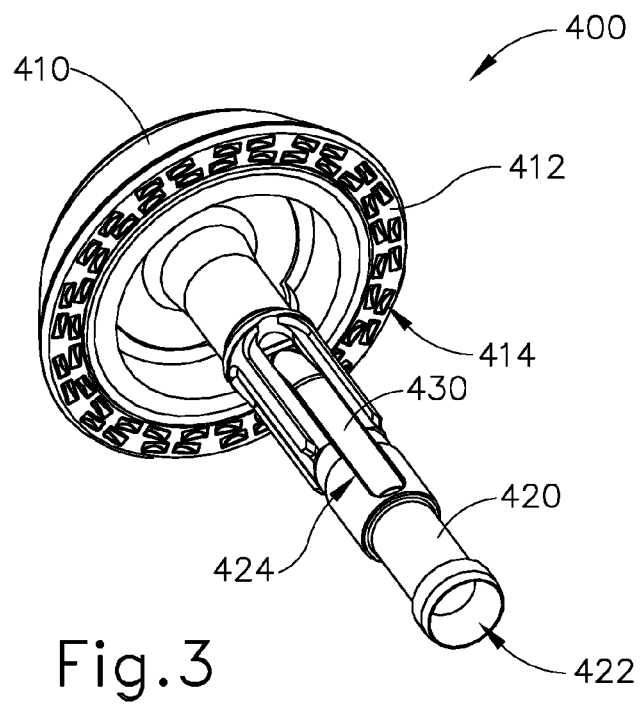
FIG. 3 depicts a perspective view of the anvil of the circular stapler of FIG. 1.

As best seen in FIG. 3, anvil (400) of the present example comprises a head (410) and a shank (420). Head (410) includes a proximal surface (412) that defines a plurality of staple forming pockets (414). Staple forming pockets (414) are arranged in two concentric annular arrays in the present example. Staple forming pockets (414) are configured to deform staples as the staples are driven into staple forming pockets (414) (e.g., deforming a generally "U" shaped staple into a "B" shape as is known in the art). Shank (420) defines a bore or lumen (422) and includes a pair of pivoting latch members (430) positioned in bore (422). Each latch member (430) includes features that allows anvil (400) to be removably secured to a trocar (330) of stapling head assembly (300) as will be described in greater detail below. It should be understood, however, that anvil (400) may be removably secured to a trocar (330) using any other suitable components, features, or techniques.

Figure 4:
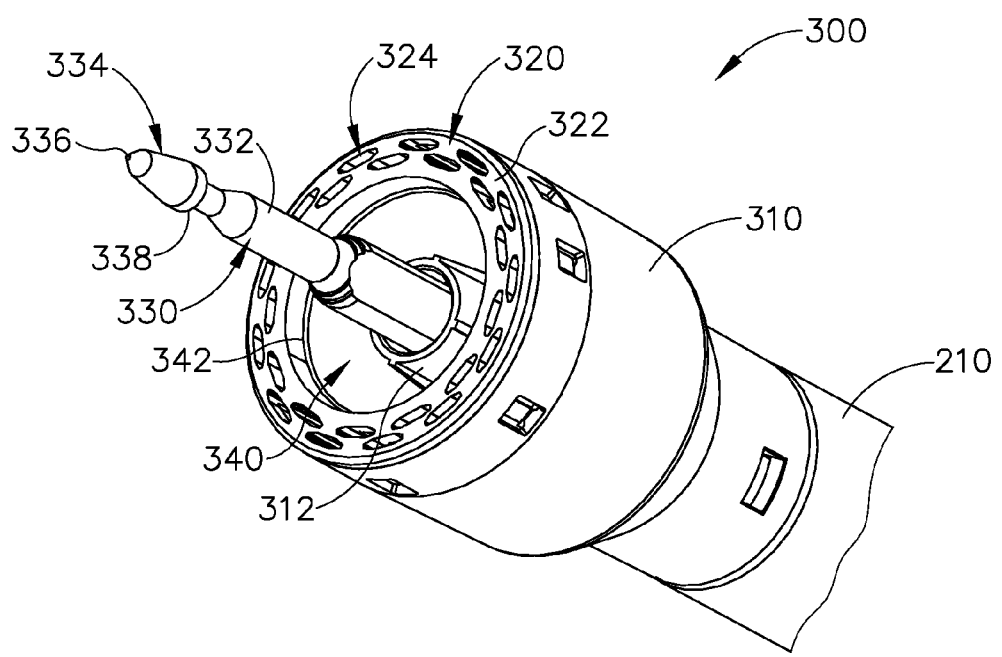
FIG. 4 depicts a perspective view of the stapling head assembly of the circular stapler of FIG. 1.
Figure 5:
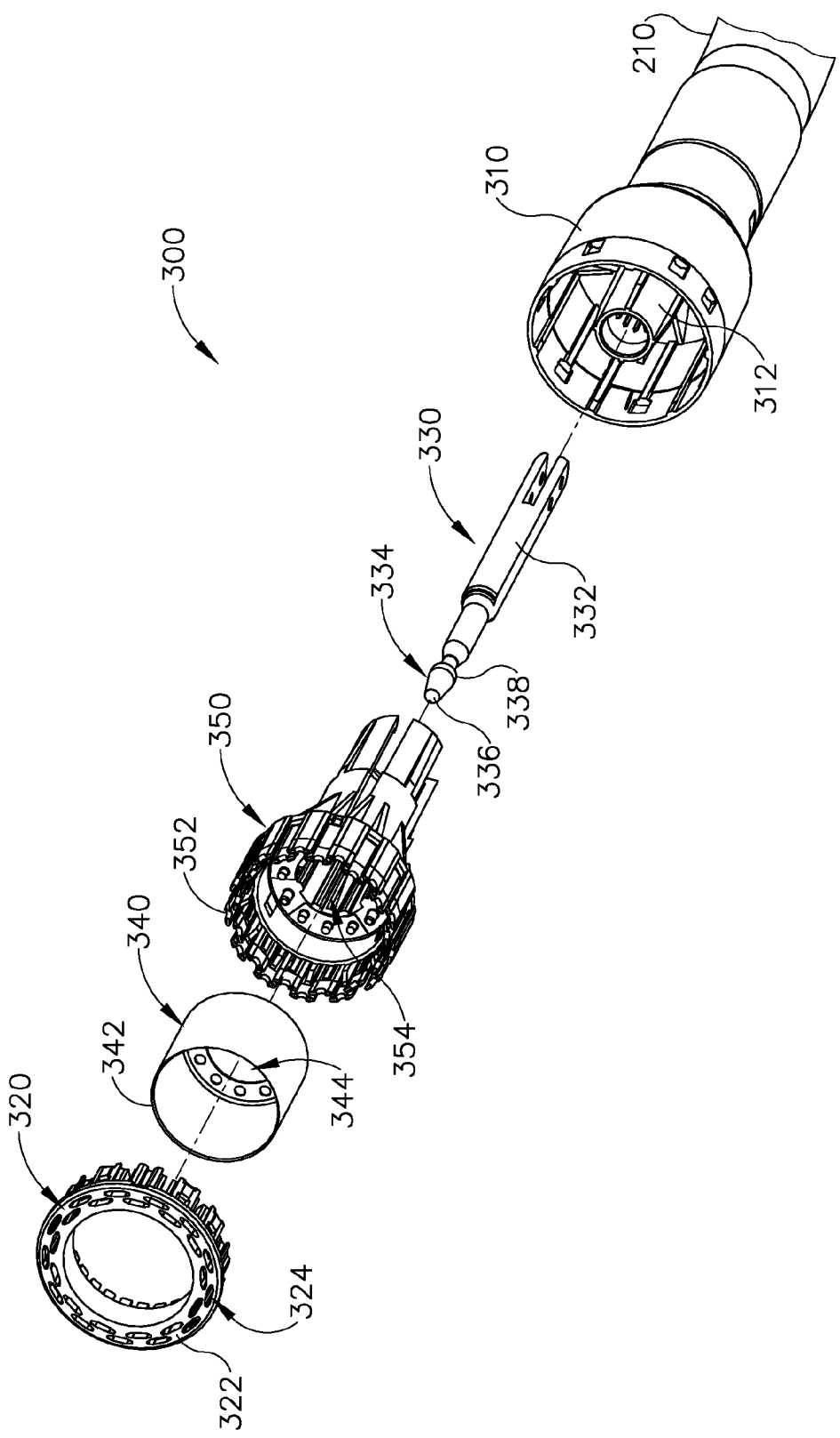
FIG. 5 depicts an exploded perspective view of the stapling head assembly of FIG. 4.

Stapling head assembly (300) is located at the distal end of shaft assembly (200). As shown in FIGS. 1-2, anvil (400) is configured to removably couple with shaft assembly (200), adjacent to stapling head assembly (300). As will be described in greater detail below, anvil (400) and stapling head assembly (300) are configured to cooperate to manipulate tissue in three ways, including clamping the tissue, cutting the tissue, and stapling the tissue. As best seen in FIGS. 4-5, stapling head assembly (300) of the present example comprises a tubular casing (310) housing a slidable staple driver member (350). A cylindraceous inner core member (312) extends distally within tubular casing (310). Tubular casing (310) is fixedly secured to an outer sheath (210) of shaft assembly (200), such that tubular casing (310) serves as a mechanical ground for stapling head assembly (300).

Trocar (330) is positioned coaxially within inner core member (312) of tubular casing (310). Trocar (330) is operable to translate distally and proximally relative to tubular casing (310) in response to rotation of a knob (130) located at the proximal end of handle assembly (100). Trocar (330) comprises a shaft (332) and a head (334). Head (334) includes a pointed tip (336) and an inwardly extending proximal surface (338). Head (334) and the distal portion of shaft (332) are configured for insertion in bore (422) of anvil (420). Proximal surface (338) is configured to complement features of latch members (430) to provide a snap fit between anvil (400) and trocar (330).

Staple driver member (350) is operable to actuate longitudinally within tubular casing (310) in response to activation of motor (160) as will be described in greater detail below. Staple driver member (350) includes two distally presented concentric annular arrays of staple drivers (352). Staple drivers (352) are arranged to correspond with the arrangement of staple forming pockets (414) described above. Thus, each staple driver (352) is configured to drive a corresponding staple into a corresponding staple forming pocket (414) when stapling head assembly (300) is actuated. Staple driver member (350) also defines a bore (354) that is configured to coaxially receive core member (312) of tubular casing (310).

A cylindraceous knife member (340) is coaxially positioned within staple driver member (350). Knife member (340) includes a distally presented, sharp circular cutting edge (342). Knife member (340) is sized such that knife member (340) defines an outer diameter that is smaller than the diameter defined by the inner annular array of staple drivers (352). Knife member (340) also defines an opening that is configured to coaxially receive core member (312) of tubular casing (310).

A deck member (320) is fixedly secured to tubular casing (310). Deck member (320) includes a distally presented deck surface (322) defining two concentric annular arrays of staple openings (324). Staple openings (324) are arranged to correspond with the arrangement of staple drivers (352) and staple forming pockets (414) described above. Thus, each staple opening (324) is configured to provide a path for a corresponding staple driver (352) to drive a corresponding staple through deck member (320) and into a corresponding staple forming pocket (414) when stapling head assembly (300) is actuated. It should be understood that the arrangement of staple openings (322) may be modified just like the arrangement of staple forming pockets (414) as described above. It should also be understood that various structures and techniques may be used to contain staples within stapling head assembly (300) before stapling head assembly (300) is actuated. Deck member (320) defines an inner diameter that is just slightly larger than the outer diameter defined by knife member (340). Deck member (320) is thus configured to allow knife member (340) to translate distally to a point where cutting edge (342) is distal to deck surface (322).

Figure 6:
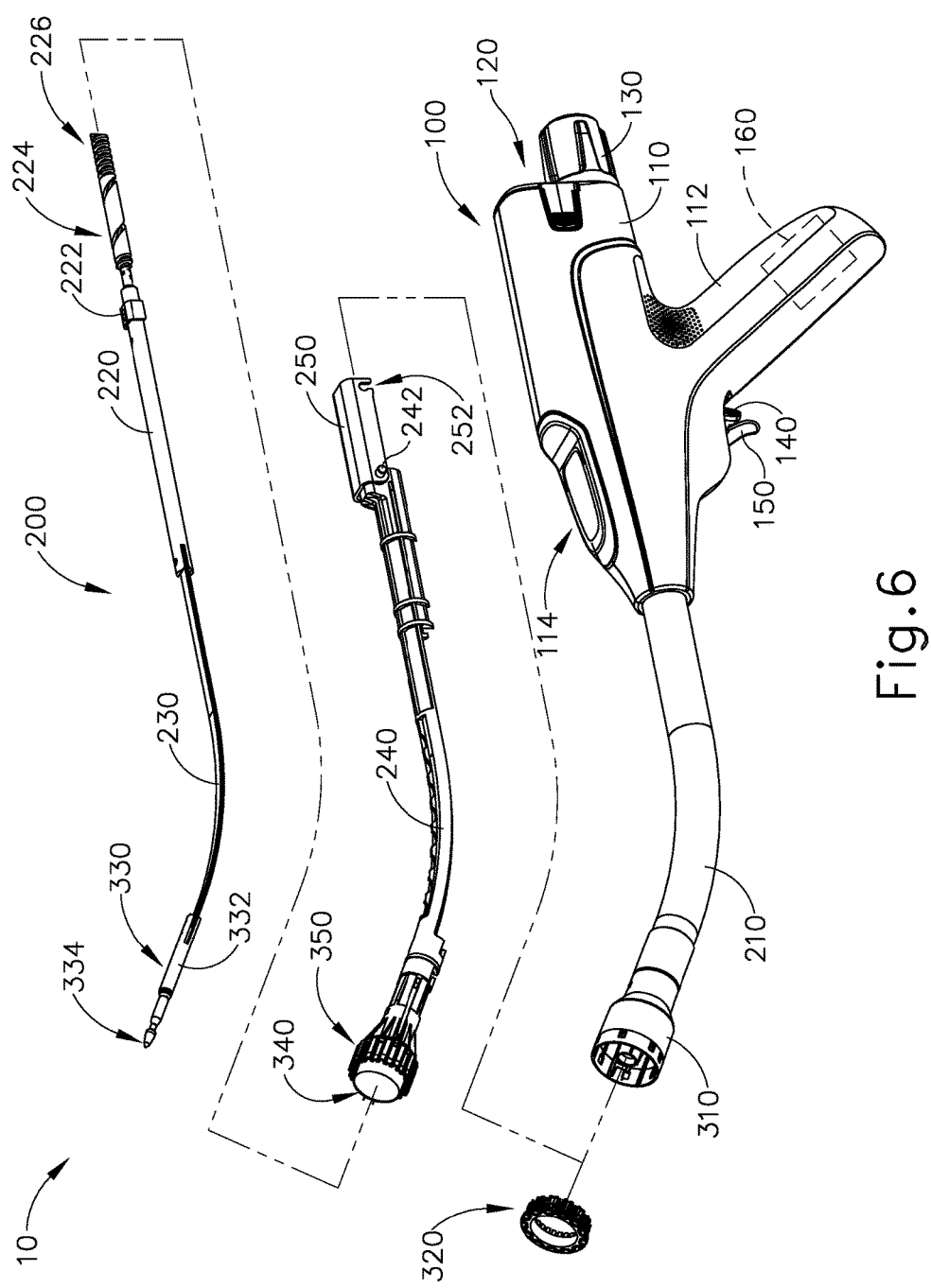
FIG. 6 depicts an exploded perspective view of the circular stapler of FIG. 1, with portions of the shaft assembly shown separately from each other.

FIG. 6 shows various components of shaft assembly (200), which extends distally from handle assembly (100) and couples components of stapling head assembly (300) with components of handle assembly (100). In particular, and as noted above, shaft assembly (200) includes an outer sheath (210) that extends between handle assembly (100) and tubular casing (310). In the present example, outer sheath (210) is rigid and includes a preformed curved section that is configured to facilitate positioning of stapling head assembly (300) within a patient's colon.

Shaft assembly (200) further includes a trocar actuation rod (220) and a trocar actuation band assembly (230). The distal end of trocar actuation band assembly (230) is fixedly secured to the proximal end of trocar shaft (332). The proximal end of trocar actuation band assembly (230) is fixedly secured to the distal end of trocar actuation rod (220), such that trocar (330) will translate longitudinally relative to outer sheath (210) in response to translation of trocar actuation band assembly (230) and trocar actuation rod (220) relative to outer sheath (210). Trocar actuation band assembly (230) is configured to flex such that trocar actuation band assembly (230) may follow along the preformed curve in shaft assembly (200) as trocar actuation band assembly (230) is translated longitudinally relative to outer sheath (210). However, trocar actuation band assembly (230) has sufficient column strength and tensile strength to transfer distal and proximal forces from trocar actuation rod (220) to trocar shaft (332). Trocar actuation rod (220) is rigid. A clip (222) is fixedly secured to trocar actuation rod (220) and is configured to cooperate with complementary features within handle assembly (100) to prevent trocar actuation rod (220) from rotating within handle assembly (100) while still permitting trocar actuation rod (220) to translate longitudinally within handle assembly (100). Trocar actuation rod (220) further includes a coarse helical threading (224) and a fine helical threading (226).

Shaft assembly (200) further includes a stapling head assembly driver (240) that is slidably received within outer sheath (210). The distal end of stapling head assembly driver (240) is fixedly secured to the proximal end of staple driver member (350). The proximal end of stapling head assembly driver (240) is secured to a drive bracket (250) via a pin (242). It should therefore be understood that staple driver member (350) will translate longitudinally relative to outer sheath (210) in response to translation of stapling head assembly driver (240) and drive bracket (250) relative to outer sheath (210). Stapling head assembly driver (240) is configured to flex such that stapling head assembly driver (240) may follow along the preformed curve in shaft assembly (200) as stapling head assembly driver (240) is translated longitudinally relative to outer sheath (210). However, stapling head assembly driver (240) has sufficient column strength to transfer distal forces from drive bracket (250) to staple driver member (350).

B. Exemplary User Input Features of Circular Stapling Instrument

As shown in FIG. 1, handle assembly (100) includes a pistol grip (112) and several components that are operable to actuate anvil (400) and stapling head assembly (300). In particular, handle assembly (100) includes knob (130), a safety trigger (140) a firing trigger (150), a motor (160), and a motor activation module (180). Knob (130) is coupled with trocar actuation rod (220) via a nut (not shown), such that coarse helical threading (224) will selectively engage a thread engagement feature within the interior of the nut; and such that fine helical threading (226) will selectively engage a thread engagement feature within the interior of knob (130). These complementary structures are configured such that trocar actuation rod (220) will first translate proximally at a relatively slow rate, then translate proximally at a relatively fast rate, in response to rotation of knob (130).

It should be understood that when anvil (400) is coupled with trocar (330), rotation of knob (130) will provide corresponding translation of anvil relative to stapling head assembly (300). It should also be understood that knob (130) may be rotated in a first angular direction (e.g., clockwise) to retract anvil (400) toward stapling head assembly (300);

and in a second angular direction (e.g., counterclockwise) to advance anvil (400) away from stapling head assembly (300). Knob (130) may thus be used to adjust the gap distance between opposing surfaces (412, 322) of anvil (400) and stapling head assembly (300) until a suitable gap distance has been achieved.

Firing trigger (150) is operable to activate motor (160) to thereby actuate stapling head assembly (300). Safety trigger (140) is operable to selectively block actuation of firing trigger (150) based on the longitudinal position of anvil (400) in relation to stapling head assembly (300). Handle assembly (100) also includes components that are operable to selectively lock out both triggers (140, 150) based on the position of anvil (400) relative to stapling head assembly (300). When triggers (140, 150) are locked out, firing trigger (150) is prevented from initiating actuation of stapling head assembly (300). Thus, trigger (150) is only operable to initiate actuation of stapling head assembly (300) when the position of anvil (400) relative to stapling head assembly (300) is within a predefined range.

In the present example, firing trigger (150) of the present example includes an integral actuation paddle, such as the paddle shown and described in U.S. patent application Ser. No. 14/751,231, entitled "Surgical Stapler with Reversible Motor," filed Jun. 26, 2015, published as U.S. Pub. No. 2016/0374666 on Dec. 29, 2016, the disclosure of which is incorporated by reference herein. The paddle is configured to actuate a switch of motor activation module (180) (FIG. 1) when firing trigger (150) is pivoted to a fired position. Motor activation module (180) is in communication with battery pack (120) and motor (160), such that motor activation module (180) is configured to provide activation of motor (160) with electrical power from battery pack (120) in response to the paddle actuating the switch of motor activation module (180). Thus, motor (160) will be activated when firing trigger (150) is pivoted. This activation of motor (160) will actuate stapling head assembly (300) as described in greater detail below.

Battery pack (120) is operable to provide electrical power to a motor (160) as noted above. Battery pack (120) may be removably coupled with handle assembly (100) through a snap fit or in any other suitable fashion. It should be understood that battery pack (120) and handle assembly (100) may have complementary electrical contacts, pins and sockets, and/or other features that provide paths for electrical communication from battery pack (120) to electrically powered components in handle assembly (100) when battery pack (120) is coupled with handle assembly (100). It should also be understood that, in some versions, battery pack (120) is unitarily incorporated within handle assembly (100) such that battery back (120) cannot be removed from handle assembly (100).

C. Exemplary Anastomosis Procedure with Circular Stapling Instrument

FIGS. 7-10 show an exemplary surgical procedure for providing a surgical anastomosis using instrument (10). In various instances, an anastomosis may be performed to remove a section of a patient's gastrointestinal (GI) tract. In the present example, multiple portions of a patient's colon are severed and stapled to resect a diseased portion (C') of the colon (C). The remaining severed and stapled portions of colon (C) are then anastomosed together, as discussed in further detail below.

Figure 7:
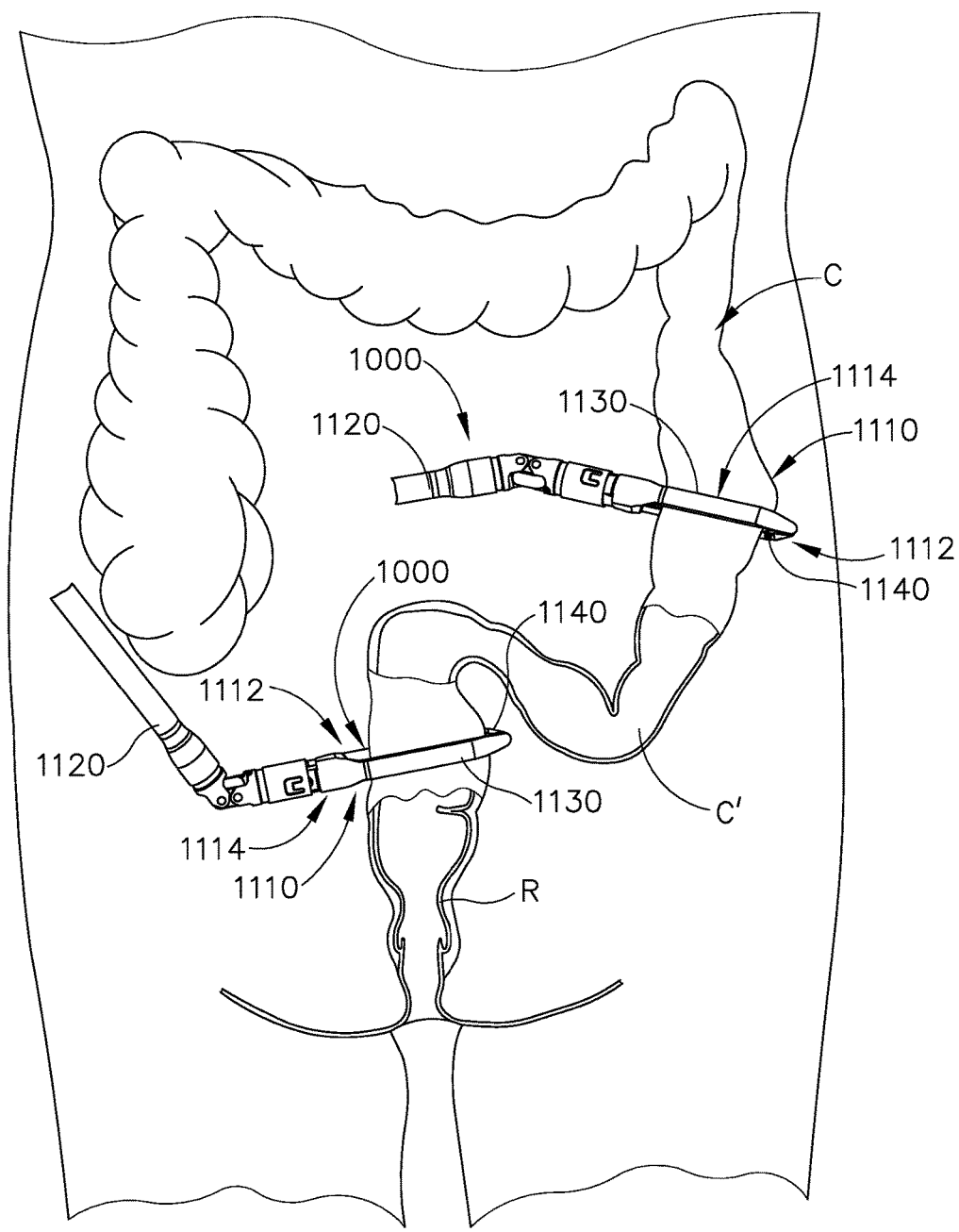
FIG. 7 depicts a schematic view of a lower portion of a patient's gastrointestinal tract, with an endocutter stapler being utilized to staple and sever the gastrointestinal tract at a first location and the endocutter stapler being utilized to staple and sever the gastrointestinal tract at a second location, thereby dividing the gastrointestinal tract into an upper portion, a transected portion, and a lower portion during a surgical procedure.

As shown in FIG. 7, multiple endocutter staplers (1000) may be inserted into a patient to sever and staple portions of the patient's colon (C). By way of example only, endocutter staplers (1000) may be constructed and operable in accordance with at least some of the teachings of U.S. Pat. No. 4,805,823, entitled "Pocket Configuration for Internal Organ Staplers," issued Feb. 21, 1989; U.S. Pat. No. 5,415,334, entitled "Surgical Stapler and Staple Cartridge," issued May 16, 1995; U.S. Pat. No. 5,465,895, entitled "Surgical Stapler Instrument," issued Nov. 14, 1995; U.S. Pat. No. 5,597,107, entitled "Surgical Stapler Instrument," issued Jan. 28, 1997; U.S. Pat. No. 5,632,432, entitled "Surgical Instrument," issued May 27, 1997; U.S. Pat. No. 5,673,840, entitled "Surgical Instrument," issued Oct. 7, 1997; U.S. Pat. No. 5,704,534, entitled "Articulation Assembly for Surgical Instruments," issued Jan. 6, 1998; U.S. Pat. No. 5,814,055, entitled "Surgical Clamping Mechanism," issued Sep. 29, 1998; U.S. Pat. No. 6,978,921, entitled "Surgical Stapling Instrument Incorporating an E-Beam Firing Mechanism," issued Dec. 27, 2005; U.S. Pat. No. 7,000,818, entitled "Surgical Stapling Instrument Having Separate Distinct Closing and Firing Systems," issued Feb. 21, 2006; U.S. Pat. No. 7,143,923, entitled "Surgical Stapling Instrument Having a Firing Lockout for an Unclosed Anvil," issued Dec. 5, 2006; U.S. Pat. No. 7,303,108, entitled "Surgical Stapling Instrument Incorporating a Multi-Stroke Firing Mechanism with a Flexible Rack," issued Dec. 4, 2007; U.S. Pat. No. 7,367,485, entitled "Surgical Stapling Instrument Incorporating a Multistroke Firing Mechanism Having a Rotary Transmission," issued May 6, 2008; U.S. Pat. No. 7,380,695, entitled "Surgical Stapling Instrument Having a Single Lockout Mechanism for Prevention of Firing," issued Jun. 3, 2008; U.S. Pat. No. 7,380,696, entitled "Articulating Surgical Stapling Instrument Incorporating a Two-Piece E-Beam Firing Mechanism," issued Jun. 3, 2008; U.S. Pat. No. 7,404,508, entitled "Surgical Stapling and Cutting Device," issued Jul. 29, 2008; U.S. Pat. No. 7,434,715, entitled "Surgical Stapling Instrument Having Multistroke Firing with Opening Lockout," issued Oct. 14, 2008; U.S. Pat. No. 7,721,930, entitled "Disposable Cartridge with Adhesive for Use with a Stapling Device," issued May 25, 2010; U.S. Pat. No. 8,408,439, entitled "Surgical Stapling Instrument with An Articulatable End Effector," issued Apr. 2, 2013; and U.S. Pat. No. 8,453,914, entitled "Motor-Driven Surgical Cutting Instrument with Electric Actuator Directional Control Assembly," issued Jun. 4, 2013. The disclosure of each of the above-cited U.S. patents is incorporated by reference herein.

In the example shown, endocutter staplers (1000) are inserted into the body laparoscopically via respective trocars. Endocutter stapler (1000) comprises a shaft (1120) and an end effector (1110) extending from the shaft (1120). End effector (1110) comprises a first jaw (1112) and a second jaw (1114). First jaw (1112) comprises a staple cartridge (1140). Staple cartridge (1140) is insertable into and removable from first jaw (1112), though some variations may provide a staple cartridge that is not removable from (or at least readily replaceable from) first jaw (1112). Second jaw (1114) comprises an anvil (1130) that is configured to deform staples ejected from staple cartridge (1140). Second jaw (1114) is pivotable relative to first jaw (1112), though some variations pay provide first jaw (1112) as being pivotable relative to the second jaw (1114). Endocutter staplers (1000) may be configured ad operable in accordance with at least some of the teachings of U.S. Pub. No. 2013/0168435, entitled "Surgical Stapling Instrument with an Articulatable End Effector," published Jul. 4, 2013, issued as U.S. Pat. No. 9,138,225 on Sep. 22, 2015, the disclosure of which is incorporated by reference. While end effector (1110) is straight and is thus configured to apply a straight line of staples (185) in the present example, in other examples end effector (1110) may be curved and may thus apply a curved line of staples (185).

Figure 8:
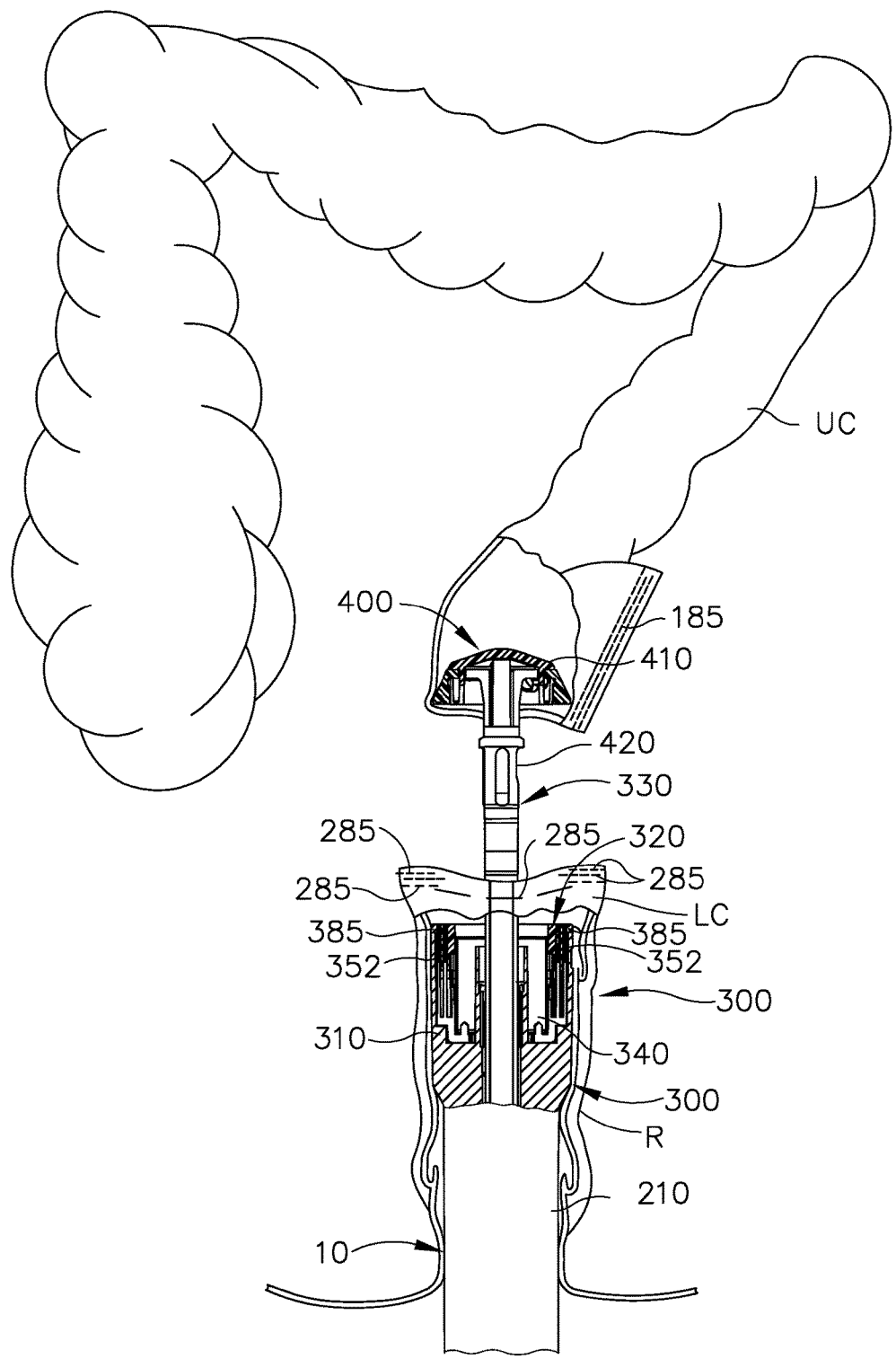
FIG. 8 depicts a schematic view of the gastrointestinal tract of FIG. 7 during another step of the surgical procedure of FIG. 7, showing the anvil of FIG. 3 positioned in the upper portion of the gastrointestinal tract and the stapling head assembly of FIG. 4 positioned in the lower portion of the gastrointestinal tract, with the anvil and the stapling head assembly and adjacent regions of the gastrointestinal tract shown in cross-section.
Figure 9:
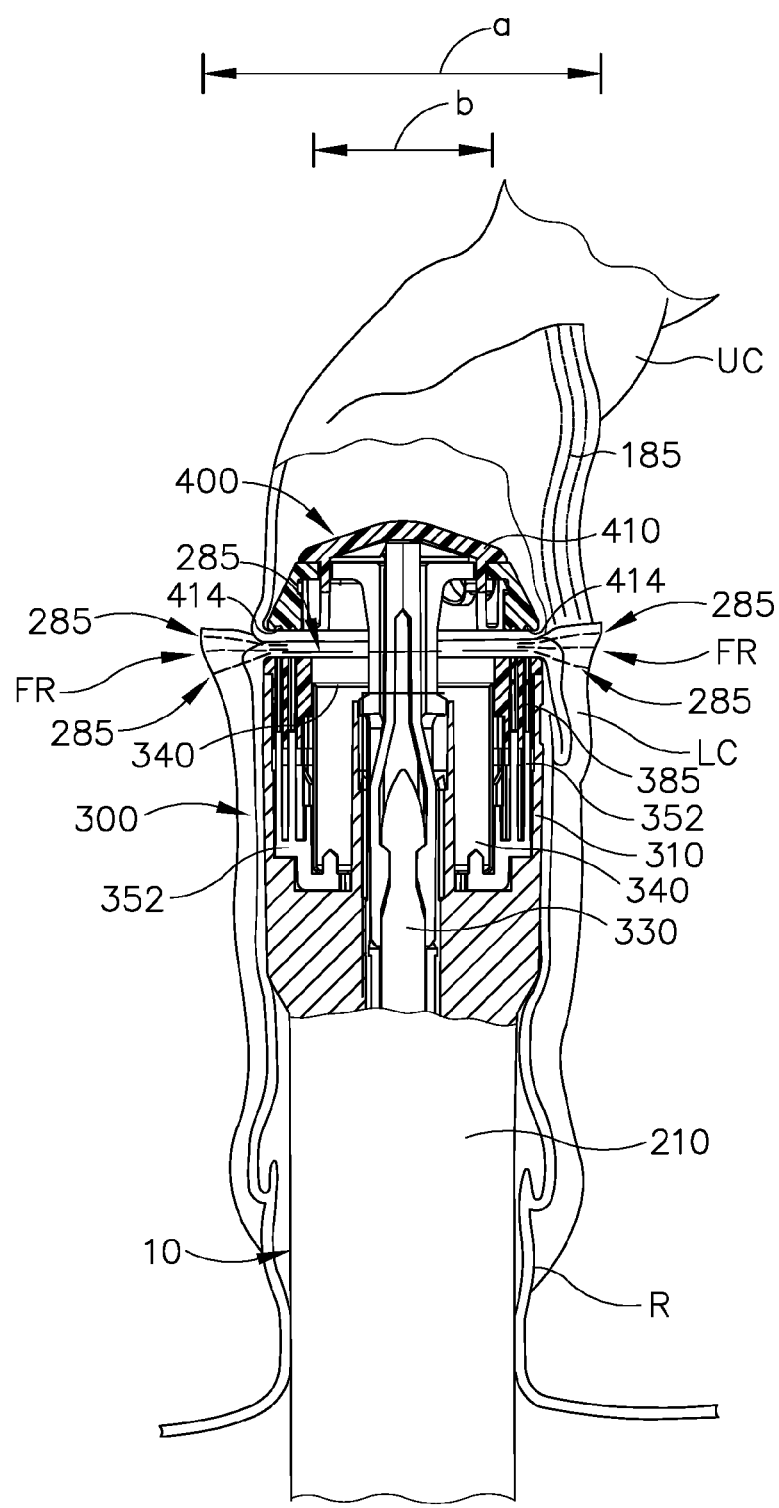
FIG. 9 depicts a schematic view of the gastrointestinal tract of FIG. 7 during another step of the surgical procedure of FIG. 7, showing the upper portion and the lower portion of the patient's gastrointestinal tract being compressed between the anvil and the stapling head assembly of the circular stapler of FIG. 1, with the anvil and the stapling head assembly and adjacent regions of the gastrointestinal tract shown in cross-section.
Figure 10:
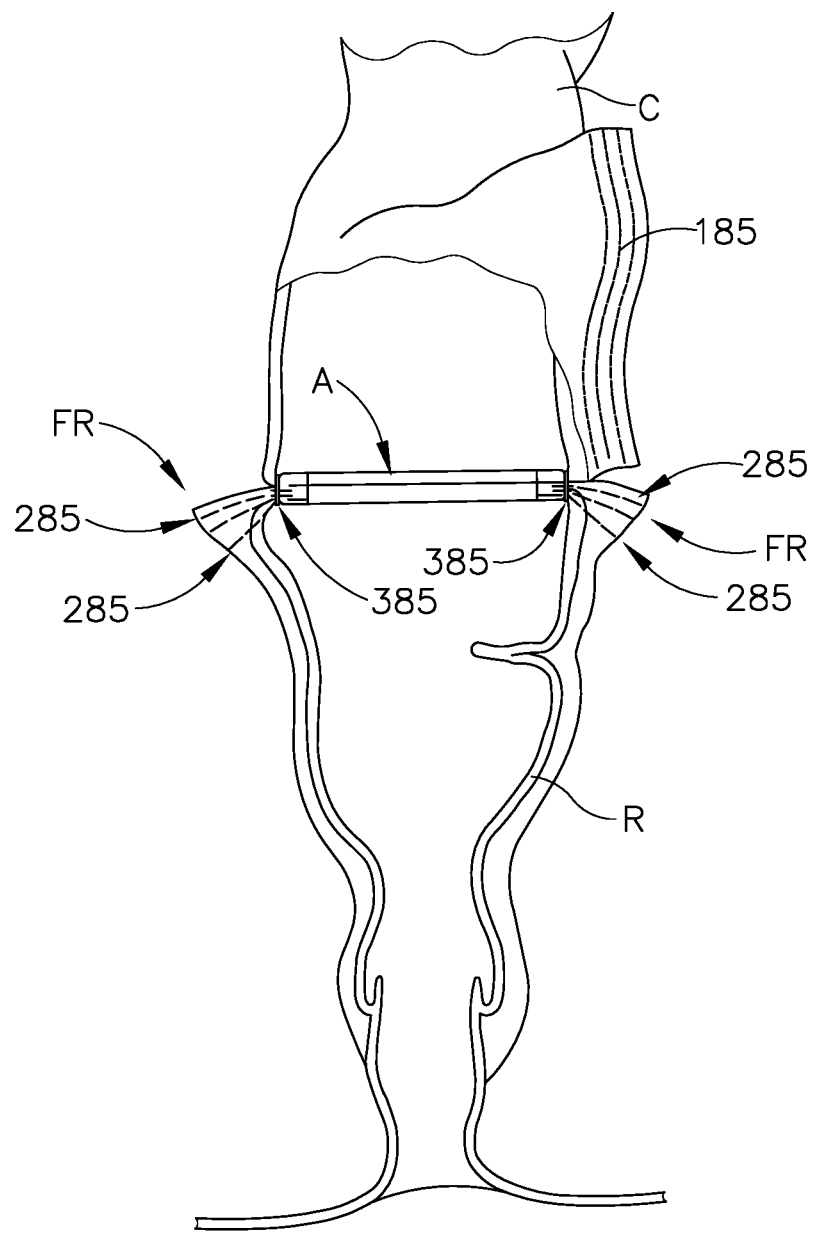
FIG. 10 depicts a schematic view of the gastrointestinal tract of FIG. 7 upon completion of the surgical procedure of FIG. 7, with the upper and lower portions of the patient's gastrointestinal tract joined by staples deployed from the circular stapler of FIG. 1, providing an anastomosis between the upper and lower portions of the patient's gastrointestinal tract, with the anastomosis and adjacent regions of the gastrointestinal tract shown in cross-section.

Anvil (1130) of endocutter stapler (1000) can be opened such that anvil (1130) and staple cartridge (1140) of endocutter stapler (1000) are positioned relative to the patient's colon (C). When anvil (1130) is moved into a closed position, anvil (1130) clamps the colon (C) against staple cartridge (1140). Turning now to FIG. 7, endocutter stapler (1000) can be operated to sever and staple the colon (C) at a first, or upper, location. In the example shown, three linear rows of staples (185) are implanted on the upper side of the severed upper portion (UC) of colon (C) and three rows of the staples (185) are implanted in the adjacent region of the diseased portion (C') of the colon (C). The same endocutter stapler (1000) (if reloaded with another cartridge (1140)), or another endocutter stapler (1000), can be operated to sever and staple the colon (C) at a second, or lower, location. In the present example, three linear rows of staples (285) implanted on the lower side of the severed lower portion (LC) of the colon (C) and three rows of staples (285) are implanted in the adjacent region of the diseased portion (C') of the colon (C). However, in other examples, other suitable configurations of staples may be implanted onto the upper portion (UC) and/or the lower portion (LC) of the colon (C). Once the colon (C) has been transected and stapled at the upper location and the lower location, the diseased portion (C') of the colon can be removed from the patient, as illustrated in FIGS. 8-10.

Referring again to FIGS. 8-9, circular stapler (10) may be utilized to anastomose the upper portion (UC) and the lower portion (LC) of the colon (C). An operator inserts a portion of shaft (210) and stapling head assembly (300) into the rectum (R) of the patient into the lower portion (LC) of the colon (C). In the example shown, a user then inserts trocar (330) through the rows of staples (285). Trocar (330) of circular stapler (10) may then be positioned in the upper portion of the colon C. In various instances, the sidewall of the upper portion of the colon C can be incised and trocar (330) can then be positioned inside the upper portion. Anvil (400) may then be directed into the upper portion of the colon (C) and connected to trocar (330) in the manner discussed above and as shown in FIG. 8.

The operator may then draw anvil (400) toward stapling head assembly (300), in the manner described above (e.g., utilizing knob (130), thus also drawing the upper colon portion (UC) toward the lower colon portion (LC). The operator may then retract trocar (330) until the tissue of the upper colon portion (UC) and the lower colon portion (LC) are compressed against deck (320) as shown in FIG. 9. It should also be understood that knob (130) may be rotated in a first angular direction (e.g., clockwise) to retract anvil (400) toward stapling head assembly (300); and in a second angular direction (e.g., counterclockwise) to advance anvil (400) away from stapling head assembly (300). Knob (130) may thus be used to adjust the gap distance between opposing surfaces of anvil (400) and stapling head assembly (300) until a suitable gap distance has been achieved, such as in the manner discussed in U.S. patent application Ser. No. 14/751, 506, published as U.S. Pub. No. 2016/0374670 on Dec. 29, 2016, the disclosure of which is incorporated by reference herein. As shown in FIG. 9, flap regions (FR) are formed in the lower portion (LC) of the colon (C) as anvil (400) is drawn toward stapling head assembly (300). These flap regions (FR) extend outwardly from the region of tissue compressed between anvil (400) and stapling head assembly (300).

As discussed above, stapling head assembly (300) is configured to apply annular arrays of staples (385) in the tissue captured between anvil (400) and stapling head assembly (300). Knife member (340) is advanced toward anvil (440) to sever the tissue positioned radially inwardly with respect to the annular arrays of staples (385) applied by circular stapling instrument (10). After the staples (385) have been fired and tissue has been severed, anvil (400) and stapling head assembly (300) may together be withdrawn from the patient's rectum (R). The incision that was used to insert anvil (400) into the upper portion (UC) of the colon (C) may be closed via suturing or using any other suitable technique.

As shown in FIG. 10, the upper portion (UC) of the colon (C) and the lower portion (LC) of the colon (C) are held together by the annular array of staples (385) deployed by circular stapling instrument (10). The deployed annular array of staples (385) forms an anastomosis (A) that allows fluid tight communication from the upper portion (UC) of the colon (C) to the lower portion (LC) of the colon (C). Some of staples (285) that were deployed by endocutter stapler (1000) will be removed with the tissue that was transected by knife member (340) during actuation of stapling head assembly (300). However, in this example, there are some staples (285) remaining in the outwardly projecting flap regions (FR) in the lower portion (LC) of the colon (C), outside of the anastomosis (A). This is due to the fact that the flap regions (FR) define a width (a) that is substantially greater than the diameter (b) of knife member (340), as best seen in FIG. 9. The flap regions (FR) may nevertheless remain sealed by those remaining staples (285).

II. Exemplary Apparatus and Methods for Radially Bunching a Bodily Lumen

In some instances, staples (385) that were deployed by circular stapling instrument (10) may overlap with at least some of staples (285) that were deployed by endocutter stapler (1000) in the procedure described above with reference to FIGS. 7-10. Such overlap may prevent proper formation of staples (385), which may compromise the integrity of anastomosis (A) in the long term. In addition or in the alternative, at least some of staples (285) that were deployed by endocutter stapler (1000) may interfere with compression of tissue between anvil (400) and deck member (320) and/or the traversal of knife member (340) through the tissue, which may also compromise the integrity of anastomosis (A) in the long term. Furthermore, there may be instances where the seal provided by staples (285) in flap regions (FR) of the lower portion (LC) of the colon (C) may eventually fail over time. It may therefore be desirable to provide features that prevent the outward extension of flap regions (FR) and position all of staples (285) and flap regions (FR) within the diameter (b) of knife member (340). Various examples of such features will be described in greater detail below.

A. Barbed Cinching Member with Cylindraceous Anvil

FIGS. 11-16E show features that may be used to prevent the outward extension of flap regions (FR) and position all of the tissue at the severed end of lower colon portion (LC) within the diameter (b) of knife member (340). In particular, FIGS. 11-16E show a bendable cinching member (500) that may be used to contract a bodily lumen such as the colon (C) inwardly, while forming an angularly spaced array of pleats in the bodily lumen. As best seen in FIG. 11, bendable cinching member (500) includes a slot (502) having a locking portion (506), a pulling end (504) with a tapered portion (508), ridges (510) configured to mate with locking portion (506), and barb features (512) separated by connecting portions (514). Connecting portions (514) and pulling end (504) are both made of flexible material such that tapered portion (508) may bend to travel through slot (502)

Tapered portion (508) is narrower compared to the remaining portion of pulling end (504) in order to better allow an operator to guide pulling end (504) within the confines of slot (502). As will be described in greater detail below, pulling end (504) is configured to enter slot (502) to allow ridges (510) to engage locking portion (506), thereby preventing pulling end (504) and tapered portion (508) from exiting slot (502) along a direction that is opposite to the direction along which pulling end (504) entered slot (502). By way of example only, locking portion (506) may include a pawl feature that ratchets along ridges (510) as pulling end (504) traverses slot (502), similar to an arrangement found in a conventional cable tie or zip tie. When ridges (510) engage locking portion (506), barb features (512) and connecting portions (514) will define a loop configured to encompass a bodily lumen, such as colon (C), when forming the loop. The farther pulling end (504) travels through slot (502), the smaller the loop becomes. Locking portion (506) will cooperate with ridges (510) to hold cinching member (500) in a cinched configuration, thereby holding the lower colon portion (LC) in a bunched-up, pleated configuration as described below.

FIGS. 12-14 show barb feature (512) of the present example on greater detail. As shown, barb feature (512) has a base (520) integrated with connection portions (514), a pair of upper angled arms (518), a pair of lower angled arms (519), and a pair of connecting arms (522). Connecting arms (522) are fixed to base (520) and provide a connection between upper angled arms (518) and lower angled arms (519). However, connection arms (522) are merely optional. Additionally, base (520) and connecting portions may be replaced with a traditional suture. Both pairs of upper angled arms (518) and lower angled arms (519) extend from connecting arms (522) to form a piercing tip (526). Piercing tip (526) connects to an inclined face (524) and a vertical face (528). As will be described in greater detail below, piercing tip (526), inclined face (524) and vertical face (528) are designed to work in tandem to form a barb that pierces and anchors to tissue such as the tissue of the colon (C). As piercing tip (526) pierces the colon (C), upper angled arms (518) and lower angled arms (519) contact the outer surface of the colon (C), forming pleats (534) similar to those formed by a conventional purse string suture arrangement. While the current example shows only four barb features (512), it should be understood that cinching member (500) may have any desired number of barbed features (512).

Barb features (512) of the present example are designed in such a way that connecting portions (514) are unitarily coupled to pulling end (504). Therefore, as pulling end (504) travels through slot (502) in order for ridges (510) to engage locking portion (506), pulling end (504) will develop a tail extending from the loop configured to encompass a bodily lumen such as the colon (C). In this example, ridges (510) are integral with pulling end (504).

Alternatively, as shown in FIG. 15, barb features (512) may be designed in such a way as to allow pulling end (504) to not be unitarily coupled to connecting portions (514) and barb features (512). In this example, retainers (530) extend from upper angled arms (518) and lower angled arms (519). Retainers (530), upper angled arms (518), lower angled arms (519), and base (520) together define a retaining gap (532). Retaining gap (532) houses pulling end (504) while allowing pulling end (504) to travel relative to connecting portions (514), barb features (512), and slot (502). However, pulling end (504) is still sufficiently contained within barb feature (512) to impart of force on barb features (512) to force barb features (512) and connecting portions (514) to define a loop while pulling end (504) is traveling through slot (502). However, since pulling end (504) is allowed to slide with respect to barb features (512), eventually as pulling end (504) travels through slot (502), pulling end (504) will disconnect from the rest of cinching member (500) leaving no tail at the end of the loop. In this example, ridges (510) may be integral with connecting portions (514) instead of pulling end (504) in order to ensure connecting portions (514) and barb features (512) remain in the newly formed loop.

Figure 16A:
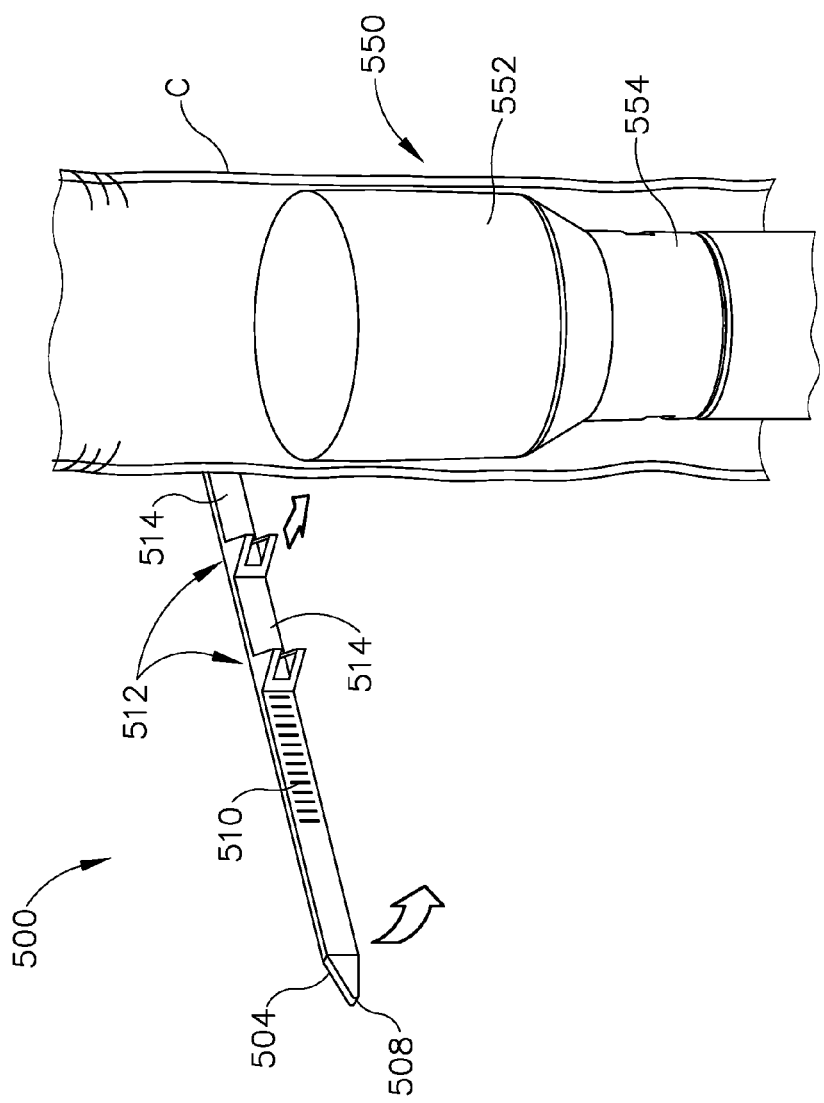
FIG. 16A depicts a partial cross-sectional perspective view of the barbed cinching member of FIG. 11 positioned adjacent to a colon, with an exemplary cylindraceous anvil inside the colon, and with the barbed cinching member in a straight configuration.

FIGS. 16A-16E show cinching member (500) being wrapped about a colon (C). First, as shown in FIG. 16A, anvil assembly (550) is inserted transanally into the colon (C). Anvil assembly (550) of this example comprises a cylindraceous anvil head (552) that is positioned on the distal end of a shaft (554). In some other variations, stapling instrument (10) is used in place of anvil assembly (550). In particular, shaft assembly (200) of instrument may serve as shaft (554) of anvil assembly (550); and the outer surface of stapling head assembly (300) may serve as anvil head (552). In the present example, once anvil head (552) is placed in the desired location, cinching member (500) is wrapped around the colon (C) at the location of anvil head (552). Anvil a head (552) provides the sufficient resistance against cinching member (500) to allow cinching member (500) to concentrically wrap around the colon (C).

Figure 16B:
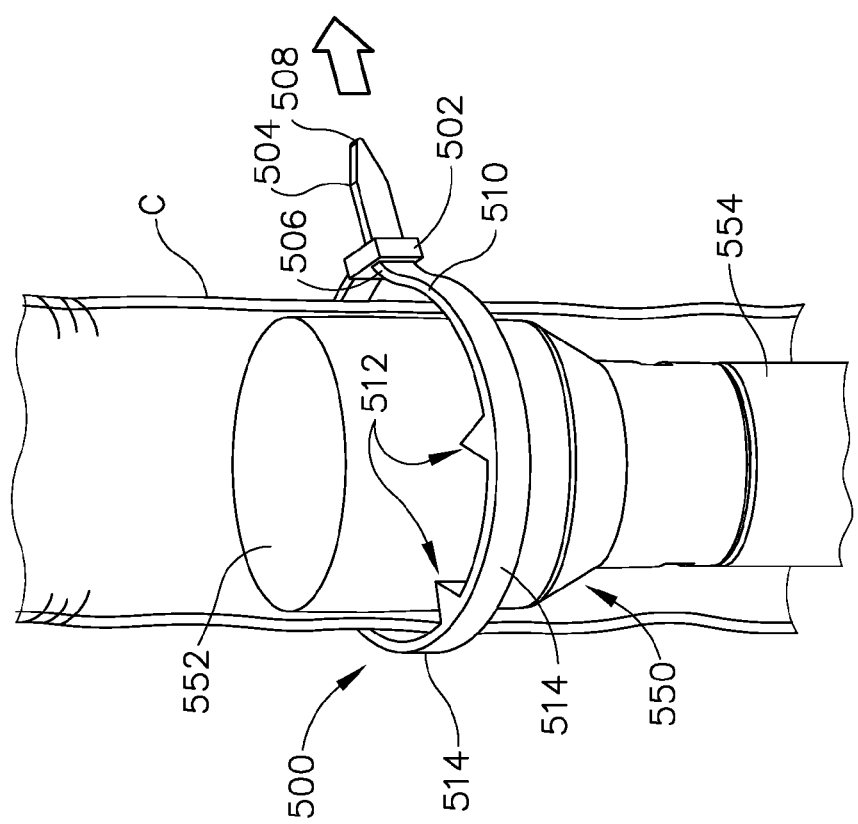
FIG. 16B depicts a partial cross-sectional perspective view of the barbed cinching member of FIG. 11 wrapped around the colon and mandrel of FIG. 16A.

As shown in FIG. 16B, tapered end (508) is inserted within slot (502) and pulled so that pulling end (504) is located within slot (502). Cinching member (500) thus forms a loop around the colon (C). At this point, movement of pulling end (504) forces barb features (512) and connecting portions (514) to encompass the colon (C) and anvil assembly (550). Each piercing tip (526) penetrates the colon (C) while inclined face (526) follows. Once vertical face (528) passes the pierced wall of the colon (C), vertical face (528) makes contact with the inner surface of the colon (C), effectively anchoring barb feature (512) to the colon (C). Anvil head (552) provides structural support to the tissue of the colon (C) to ensure that barb features (512) fully pierce the colon (C).

Figure 16C:
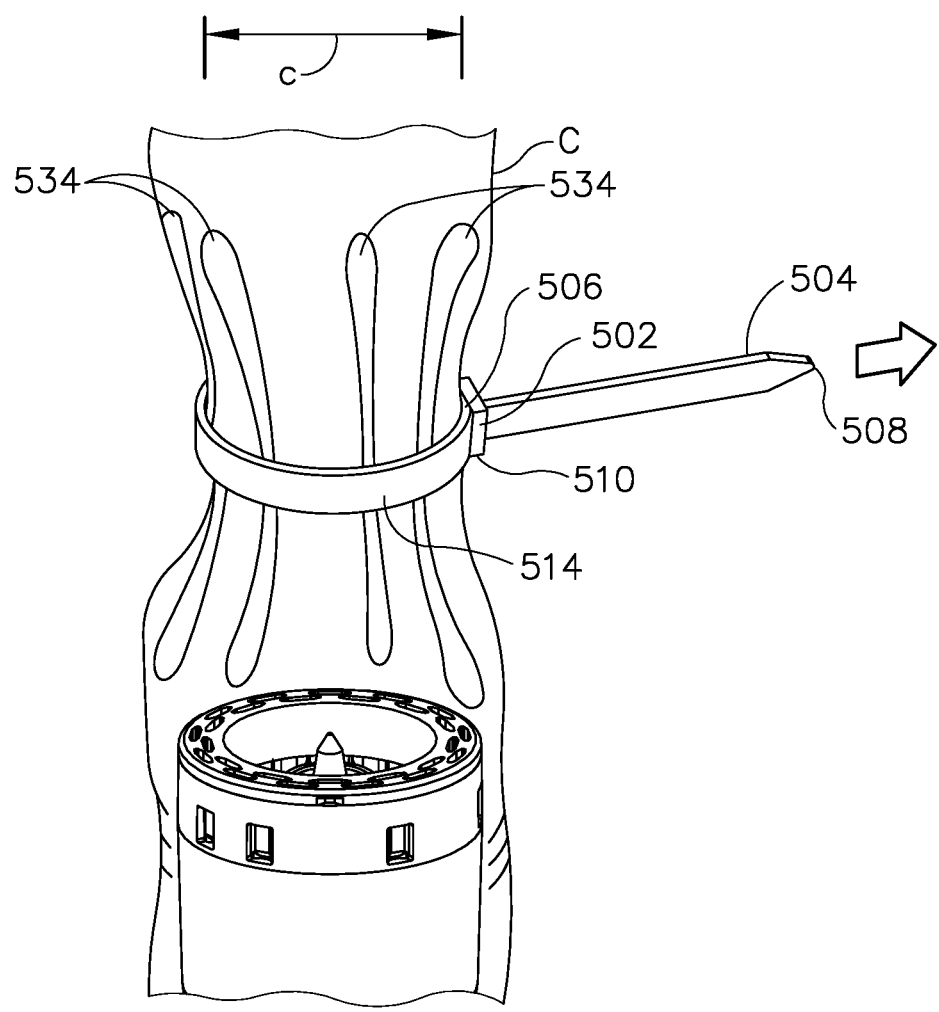
FIG. 16C depicts a perspective view of the barbed cinching member of FIG. 11 wrapped around the colon FIG. 16A, with the mandrel removed, and with the barbed cinching member cinching the colon.

As shown in FIG. 16C, once each barb feature (512) is anchored to the colon (C), anvil assembly (550) is removed from the colon (C). Pulling end (504) is then pulled further in relation to slot (502). Ridges (510) engage locking mechanism (506), preventing barb features (512) from loosening with respect with the colon (C). As pulling end (504) is further advanced in relation to slot (502), upper angled arms (518) and lower angled arms (519) further engage the colon (C) to form larger pleats (534). At this stage, the colon (C) is in a bunched-up, pleated (534) configuration. It should be understood that the reduced diameter (c) of the bunched-up region of the colon (C) is smaller than the diameter (b) of knife member (340), such that the bunched-up tissue containing pleats (534) and cinching member (500) will fit within the cylindrical plane defined by knife member (340) at this stage. In the present example, cinching member (500) is positioned at a location of the colon (C) that is between a diseased portion (C') of the colon (C) and the patient's rectum (R).

Figure 16D:
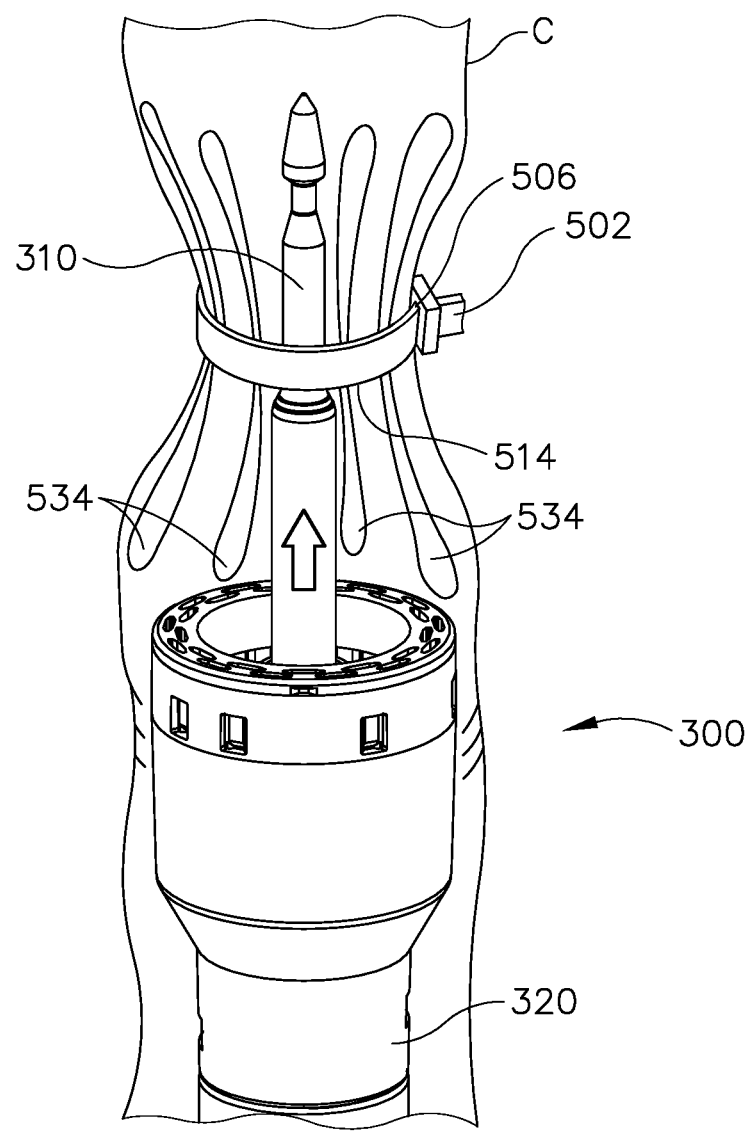
FIG. 16D depicts a perspective view of the barbed cinching member of FIG. 11 wrapped around the colon of FIG. 16A, with the stapling head assembly of FIG. 4 being positioned in the lower portion of the colon below the cinched region of the colon.

As shown in FIG. 16D, pulling end (504) is then removed (e.g., cut away) at a location near slot (502). Stapling head assembly (300) is positioned within the colon (C) just below the cinched region where cinching member (500) is located. In versions where stapling head assembly (300) is used as anvil head (552), it should be understood that stapling head assembly (300) may be advanced distally within the colon (C) to a first position for the steps shown in FIGS. 16A-16B, then retracted proximally within the colon (C) to a second position for the step shown in FIG. 16C, then advanced distally within the colon (C) to a third position for the step shown in FIG. 16D. At this stage (or right before the stage shown in FIG. 16D), the operator may use an endocutter stapler (1000) to separate an upper region of the diseased portion (C') of the colon (C) from an upper portion (UC) of the colon (C) as described above with reference to FIG. 7. However, instead of using an endocutter stapler (1000) to separate a lower region of the diseased portion (C') of the colon (C) from the lower portion (LC) of the colon (C) as described above with reference to FIG. 7, the operator may simply use a conventional cutting instrument (e.g., shears, knife, etc.) to cut the diseased portion (C') of the colon (C) from the lower portion (LC) of the colon (C), just above the bunched-up region of the colon (C) that is shown in FIG. 16D.

Figure 16E:
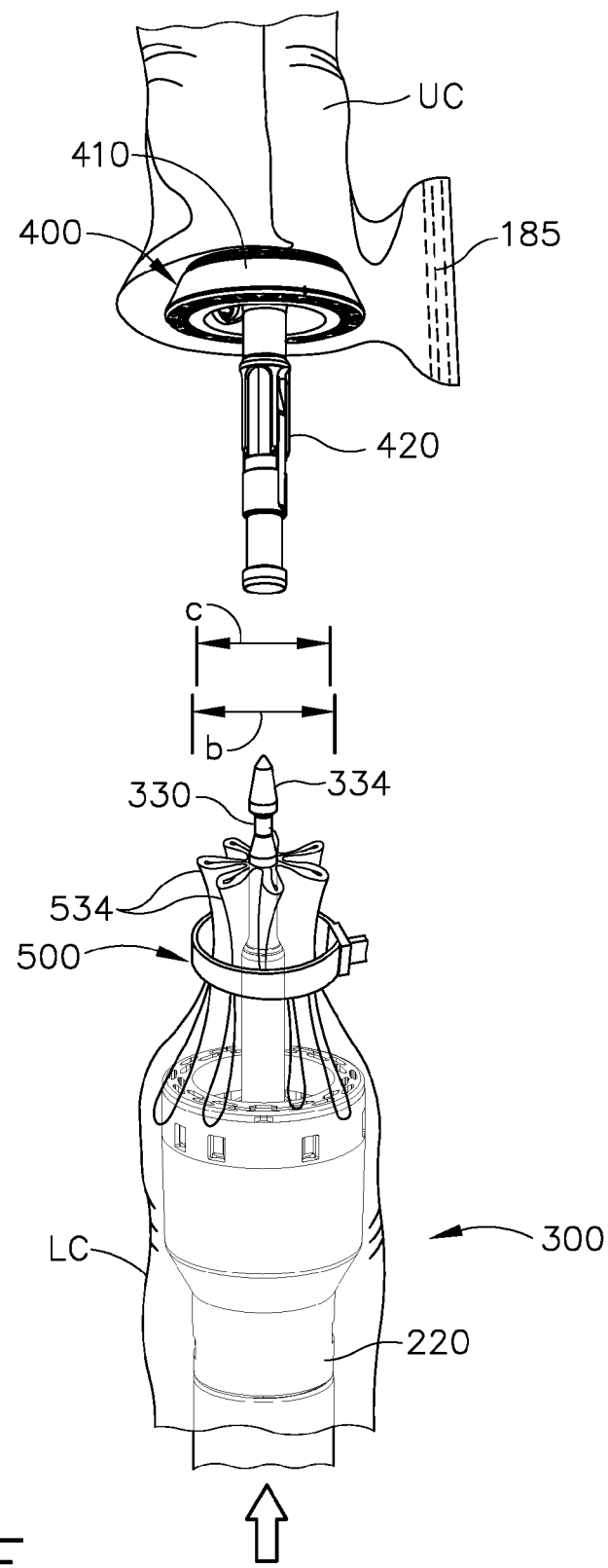
FIG. 16E depicts a perspective view of the barbed cinching member of FIG. 11 wrapped around the colon of FIG. 16A, with the stapling head assembly of FIG. 4 positioned in the lower portion of the colon below the cinched region of the colon, with the anvil of FIG. 3 positioned in an upper portion of the colon, with the upper and lower portions of the colon separated from each other.

As shown in FIG. 16E, the operator may then insert anvil (400) into the upper portion (UC) of the colon (C) as described above with reference to FIG. 8; and insert stapling head assembly (300) into the lower portion (LC) of the colon (C) as also described above with reference to FIG. 8. Trocar (330) may be advanced to a position where trocar (330) passes through the bunched-up region of the colon (C) and protrudes from the severed end of the lower portion (LC) of the colon (C). The operator may then secure shank (420) of anvil (400) to trocar (330) and clamp the adjacent regions of tissue as described above with reference to FIG. 9. As noted above, the reduced diameter (c) of the bunched-up region of the colon (C) is smaller than the diameter (b) of knife member (340), such that the bunched-up tissue containing pleats (534) and cinching member (500) will fit within the cylindrical plane defined by knife member (340) at this stage.

The operator may then actuate trigger (150) to actuate stapling head assembly (300), resulting in the stapling and severing of tissue in a similar manner as shown in FIG. 9 to form an anastomosis (A). However, due to the cinching of the tissue at the severed end of lower colon portion (LC), with the tissue and cinching member (500) being radially inward of the cut line of circular knife (340) as discussed above, all of the tissue at the severed end of lower colon portion (LC) is severed and there are no flap regions (FR) extending outwardly from the anastomosis (A) site. The severed portion of tissue including cinching member (500) may be removed by the operator via the patient's rectum.

B. Staple Array with Pull-Through Suture for Purse String Cinching

FIGS. 17-20 show additional features that may be used to prevent the outward extension of flap regions (FR) and position all of the tissue at the severed end of lower colon portion (LC) within the diameter (b) of knife member (340). In particular, FIGS. 17-20 show a staple and suture applying assembly (600) that includes anvil collar (610), a circular suture and staple housing (630), and a driver (680).

Figure 17:
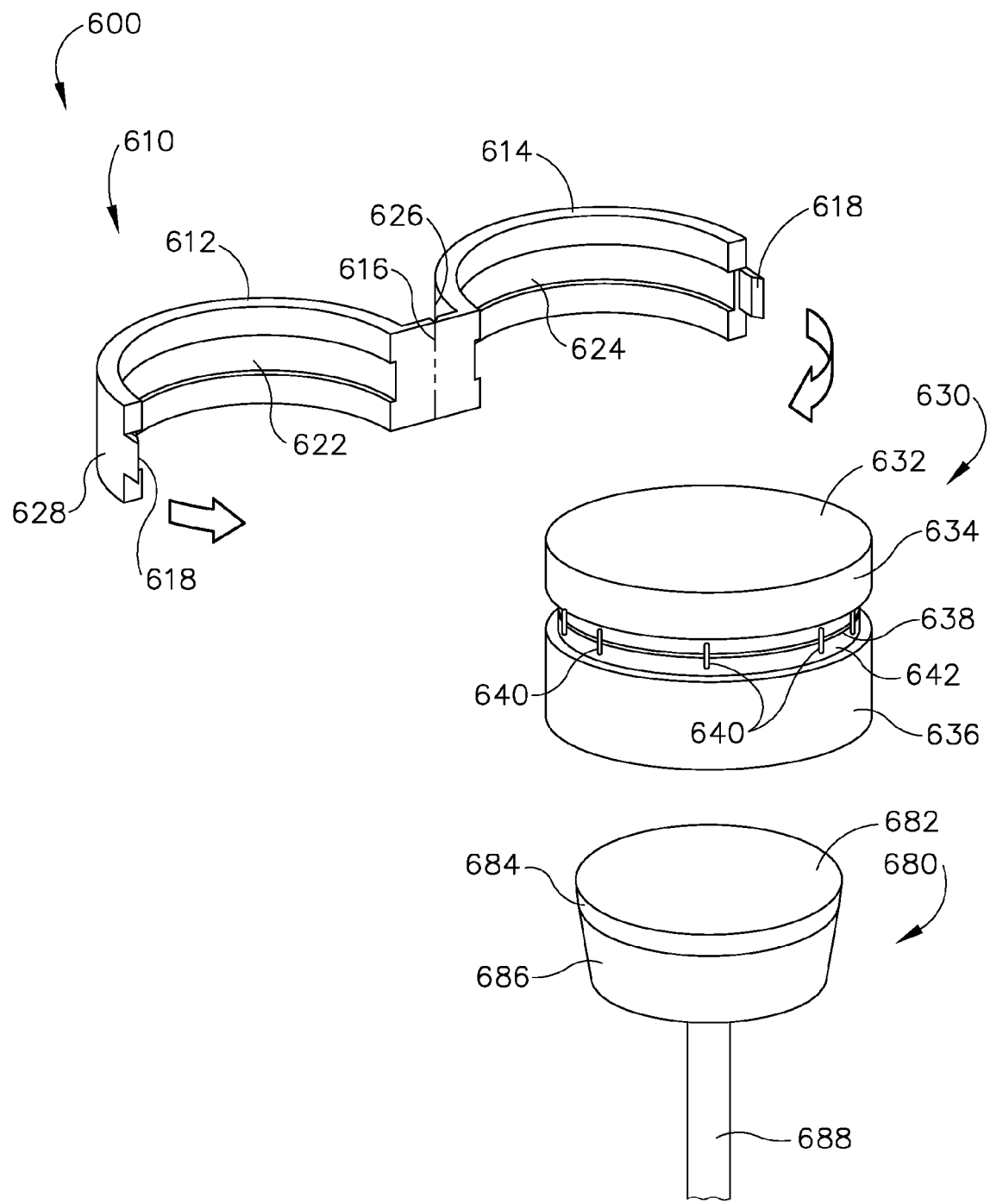
FIG. 17 depicts an exploded perspective view of an exemplary tissue stapling assembly.

As best seen in FIG. 17, anvil collar (610) includes a first half (612) and a second half (614) that are connected together via a hinge (616). First half (612) and second half (614) are configured to rotate toward and away from each other via hinge (616). First half (612) and second half (614) each contain complementary latching features (618) configured to allow first half (612) and second half (614) to selectively couple and decouple with each other. First half (612) and second half (614) may thus rotate about hinge (616) to couple or decouple with each other via latching features (618). First half (612) and second half (614) include exterior surfaces (628, 626), respectively. First half (612) and second half (614) also include interior surfaces (623, 625), respectively, that are configured to abut against the outside surface of the colon (C). First half (612) and second half (614) also include staple forming surfaces (622, 624), respectively, that are configured to form staples (640) as will be described in greater detail below.

Figure 18:
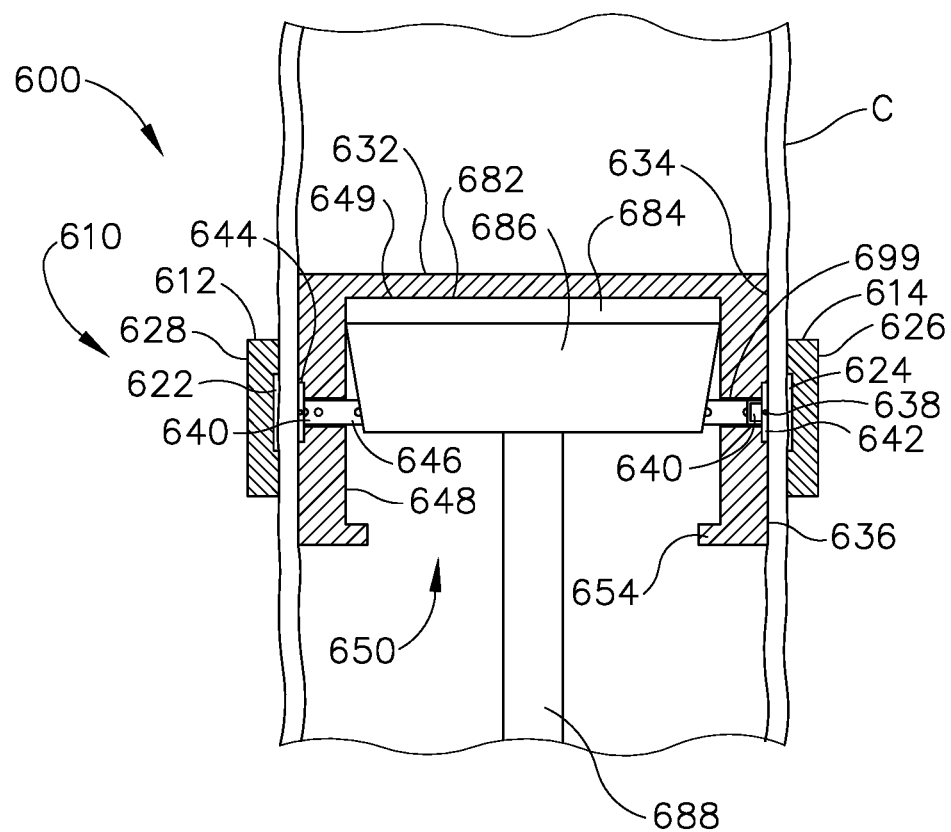
FIG. 18 depicts a cross sectional side view of the tissue stapling assembly of FIG. 17, with an anvil of the tissue tacking assembly attached to the exterior of a colon and the staple cartridge and staple driver of the tissue stapling assembly located within the colon.
Figure 19:
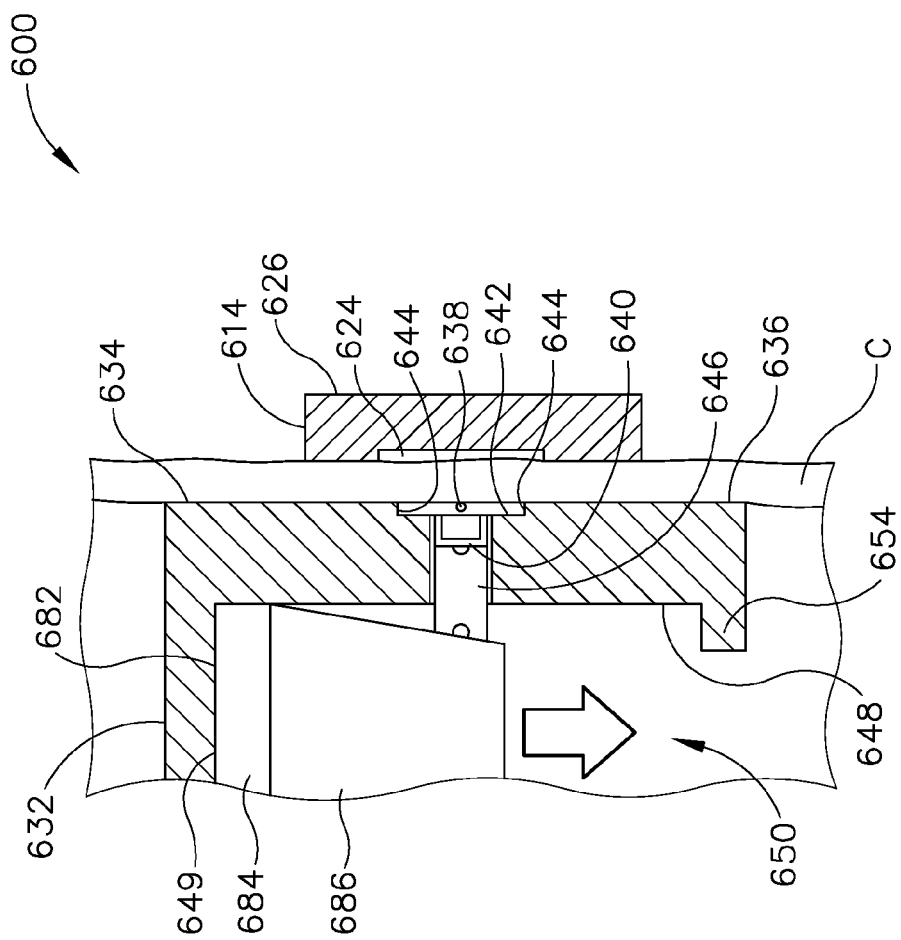
FIG. 19 depicts an enlarged cross sectional side view of the tissue stapling assembly of FIG. 17, with the anvil attached to the exterior of the colon and the staple cartridge and staple driver located within the colon.
Figure 20:
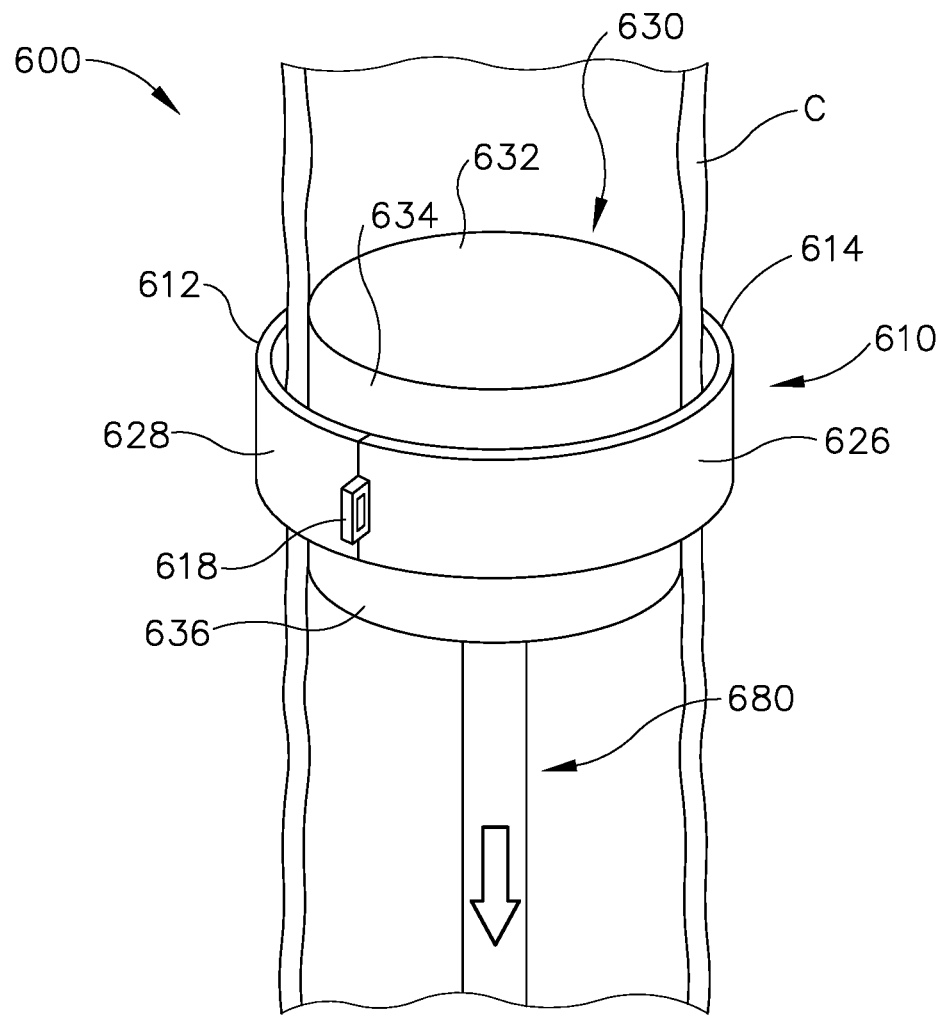
FIG. 20 depicts a partial cutaway perspective view of the tissue stapling assembly of FIG. 17 attached to the colon.

Housing (630) is configured to house staples (640) and suture (638) until driver (680) drives staples (640) into the colon (C) to thereby radially fix staples (640) and suture (638) to the inside of the colon (C). As shown in FIGS. 17-19, housing (630) includes a top surface (632), an upper grounding surface (634), a lower grounding surface (636), an annular recess (642) separating upper grounding surface (634) from lower grounding surface (636), a plurality of holes (699) angularly spaced from each other around annular recess (642), suture (638) wrapped around annular recess (642), staples (640) housed within annular recess (642), a top interior wall (649), an interior annular wall (648), an interior recess (650) defined by top interior wall (649), an interior annular wall (648), a plurality of staple drivers (646) slidably housed within holes (699), and a driver stop (654) located at the bottom of interior annular wall (648). Staple drivers (646) are each positioned to contact respective individual staples (640) before assembly (600) is actuated. As will be described below, staple drivers (646) are configured to move radially outwardly to thereby push staples (640) away from annular recess (642). Additionally, suture (638) is wrapped around annular recess (642) in such a manner that suture (638) is in contact with staples (640). Because of contact between staples (640) and suture (638), suture (638) will travel radially outwardly with staples (640) when staple drivers (646) push staples (640) radially outwardly.

Driver (680) includes a top (682), a vertical cam surface (684), an inclined cam surface (686), and a drive rod (688) extending from the bottom of inclined cam surface (686). As shown in FIGS. 18-19, interior recess (650) of housing (650) is configured to house top (682), vertical cam surface (684) and inclined cam surface (686). Drive rod (688) is configured to translate cam surfaces (684, 686) relative to housing (630). However, driver stop (654) of housing (630) is configured to contact inclined cam surface (686) when driver (680) is at a proximal position; while top interior wall (649) of circular suture and staple housing (630) is configured to contact top (682) when driver (680) is at a distal position. Housing (630) thus restricts the range of longitudinal movement of driver (680) relative to housing (630) such that driver (680) is only allowed to travel relative to housing (630) while being confined within housing (630).

As shown in FIG. 18, the operator may insert housing (630) and driver (680) transanally into the colon (C). Housing (630) is dimensioned so that grounding surfaces (634, 636) engage the sidewall of the colon (C). In some versions, surfaces (634, 636) present an outer diameter that is larger than the natural inner diameter of the colon (C), such that the colon (C) will bulge outwardly in response to housing (630) being located in the colon (C). This bulge may facilitate visualization of the longitudinal position of of housing (630) within the colon (C) from the exterior of the colon (C). In addition or in the alternative, housing (630) may include one or more light emitting features that provide transillumination through the wall of the colon (C), thereby facilitating visualization of the longitudinal position of housing (630) within the colon (C) from the exterior of the colon (C).

Once the operator has located housing (630) and driver (680) at the desired position within the colon (C), the operator may then secure anvil collar (610) about the exterior of the colon (C), in the location of housing (630). The operator may determine the location of housing (630) by visualizing a bulge in the colon (C) created by housing (630), by visualizing light emitted by housing (630) through the wall of the colon (C), or using any other suitable features or techniques. To secure anvil collar (610), the operator rotates first half (612) and second half (614) about hinge (616) to capture the colon (C) between halves (612, 614), then secures latching features (618) together. Anvil collar (610) should be located such that staple forming surfaces (622, 624) are vertically aligned with annular recess (642). This alignment ensures that staples (640) will contact staple forming surfaces (622, 624) when staples (640) are driven radially outwardly by staple drivers (646). In some versions, anvil collar (610) and surfaces (634, 636) comprises complementary features (e.g., angled surfaces, etc.) that provide camming guidance to anvil collar (610) as halves (612, 614) are pivoted to the closed position about the colon (C), thereby guiding anvil collar (610) into the proper longitudinal position relative to housing (630). Various suitable forms that such guiding features may take will be apparent to those of ordinary skill in the art in view of the teachings herein. It should also be understood that such features may be relied upon to maintain the proper longitudinal positioning of anvil collar (610) relative to housing (630) during further operation of assembly (600) as described below.

With anvil collar (610) secured to the exterior of the colon (C), and housing (630) properly located within the interior of the colon (C), staple driver (680) may be actuated downwardly by the operator pulling on driver rod (688). As the operator pulls on driver rod (688), the operator may also be gripping anvil collar (610) in order to maintain the longitudinal position of anvil collar (610) relative to the colon (C). Various suitable ways in which the operator may provide such a grounding grip on anvil collar (610) will be apparent to those of ordinary skill in the art in view of the teachings herein. Similarly, the operator may hold housing (630) in a fixed position relative to the colon (C) as the operator pulls driver rod (688) proximally. By way of example only, an outer grounding tube or sheath may be coaxially positioned about driver rod (688) and may engage housing (630) in such a way as to provide a mechanical ground to housing (630), preventing any proximal movement of housing (630) in response to proximal pulling on driver rod (688).

As shown in FIG. 19, inclined cam surface (686) makes contact with staple driver (646) as driver rod (688) is pulled proximally. Cam surface (686) thereby drives staple (640) radially outwardly through the colon (C) and against either staple forming surface (622, 624). Vertical cam surface (684) eventually contacts staple driver (646) and thereby ensures that staple driver (646) has driven staple (640) to the proper location. It should therefore be understood that driver (680) acts as a mandrel in this example, acting on all drivers (646) and staples (640) in the angular array simultaneously. Staple forming surfaces (622, 624) deform staples (640) in such a way that staples are now fixed to the colon (C). As mentioned above, suture (638) travels with staples (640) and is thereby fixed to the interior of the colon (C) by being captured between the crowns of staples (640) and the tissue of the colon (C).

Figure 21:
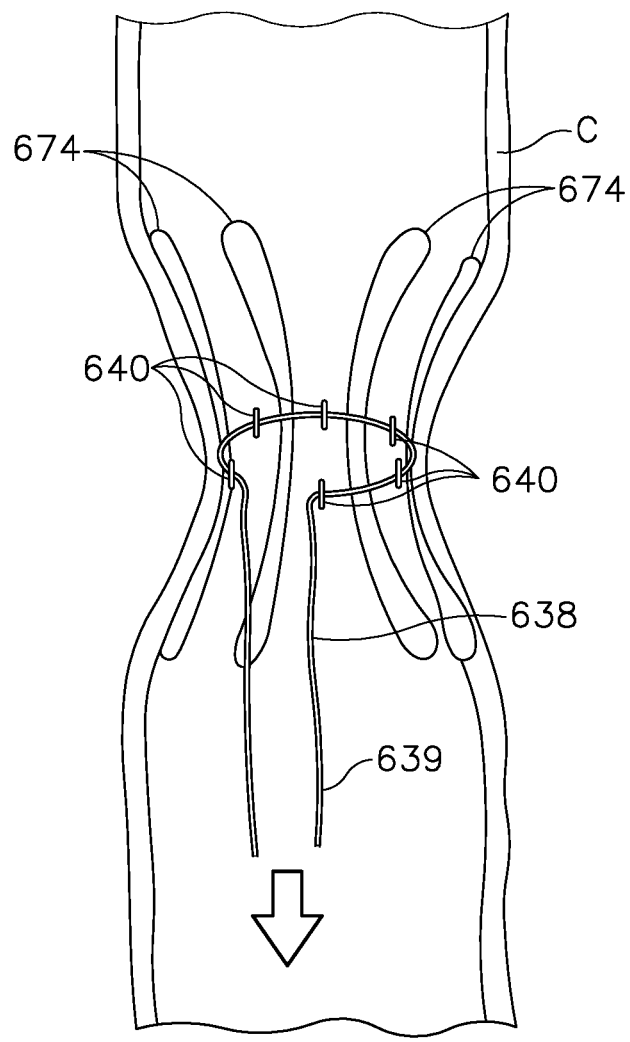
FIG. 21 depicts a perspective view of a suture and staples of the tissue stapling assembly of FIG. 17 attached to the colon, with the colon drawn in to a cinched configuration.

Anvil collar (610), housing (630), and driver (680) are then removed from the colon (C). In particular, the operator decouples latching features (618) and pivots halves (612, 614) of anvil collar (610) apart to remove anvil collar (610) from the exterior of the colon (C). The operator then simply pulls housing (630) and staple driver (680) proximally out of the colon (C) transanally. FIG. 21 shows suture (638) secured to the wall of the colon (C) via staples (640) after anvil collar (610), housing (630), and driver (680) have been removed from the colon (C). As shown, staples (640) are arranged in an annular array, such that suture (638) extends along the wall of the colon (C) in an arcuate path. In addition, the secured suture (638) provides free ends (639) that may be grasped and pulled proximally by the operator. When this is done, suture (638) and staples (640) cooperate to draw the colon (C) inwardly, forming pleats (674).

Thus, at this stage as shown in FIGS. 21-22, the colon (C) is in a bunched-up, pleated (674) configuration. It should be understood that the reduced diameter (d) of the bunched-up region of the colon (C) is smaller than the diameter (b) of knife member (340), such that the bunched-up tissue containing pleats (674), suture (638), and staples (640) will fit within the cylindrical plane defined by knife member (340) at this stage. In the present example, suture (638) and staples (640) are positioned at a location of the colon (C) that is between a diseased portion (C') of the colon (C) and the patient's rectum (R).

As also shown in FIG. 22, stapling head assembly (300) is positioned within the colon (C) just below the cinched region where suture (638) and staples (640) are located. Right before reaching the stage shown in FIG. 22, the operator uses an endocutter stapler (1000) to separate an upper region of the diseased portion (C') of the colon (C) from an upper portion (UC) of the colon (C) as described above with reference to FIG. 7. However, instead of using an endocutter stapler (1000) to separate a lower region of the diseased portion (C') of the colon (C) from the lower portion (LC) of the colon (C) as described above with reference to FIG. 7, the operator may simply use a conventional cutting instrument (e.g., shears, knife, etc.) to cut the diseased portion (C') of the colon (C) from the lower portion (LC) of the colon (C), just above the bunched-up region of the colon (C) that is shown in FIGS. 21-22.

As also shown in FIG. 22, the operator may then insert anvil (400) into the upper portion (UC) of the colon (C) as described above with reference to FIG. 8; and insert stapling head assembly (300) into the lower portion (LC) of the colon (C) as also described above with reference to FIG. 8. Trocar (330) may be advanced to a position where trocar (330) passes through the bunched-up region of the colon (C) and protrudes from the severed end of the lower portion (LC) of the colon (C). The operator may then secure shank (420) of anvil (400) to trocar (330) and clamp the adjacent regions of tissue as described above with reference to FIG. 9. As noted above, the reduced diameter (d) of the bunched-up region of the colon (C) is smaller than the diameter (b) of knife member (340), such that the bunched-up tissue containing pleats (674), suture (638), and staples (640) will fit within the cylindrical plane defined by knife member (340) at this stage.

The operator may then actuate trigger (150) to actuate stapling head assembly (300), resulting in the stapling and severing of tissue in a similar manner as shown in FIG. 9 to form an anastomosis (A). However, due to the cinching of the tissue at the severed end of lower colon portion (LC), with the tissue, suture (638), and staples (640) being radially inward of the cut line of circular knife (340) as discussed above, all of the tissue at the severed end of lower colon portion (LC) is severed and there are no flap regions (FR) extending outwardly from the anastomosis (A) site. The severed portion of tissue including suture (638) and staples (640) may be removed by the operator via the patient's rectum.

III. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus comprising: (a) a locking portion; (b) a flexible pulling portion, wherein the locking portion is configured to receive the pulling portion, wherein the pulling portion is configured to engage and translate relative to the locking portion after the locking portion has received the pulling portion; (c) a flexible body, wherein the flexible body extends from the locking portion to the pulling portion, wherein the flexible body is configured to form a loop when the pulling portion engages the locking portion, wherein the loop is configured to decrease in size in response to pulling of the pulling portion relative to the locking portion; and (d) a plurality of barb features extending laterally from the body, wherein the barb features are configured to engage a tubular region of tissue and thereby form pleats in the tubular region of tissue.

Example 2

The apparatus of Example 1, wherein the locking portion is configured to restrict translation of the pulling portion to a single direction.

Example 3

The apparatus of any one or more of Examples 1 through 2, wherein at least one barb feature in the plurality of barb features comprise a first pair of angled arms.

Example 4

The apparatus of Example 3, wherein at least one barb feature in the plurality of barb features comprise a first piercing tip located at the end of the first pair of angled arms, wherein the first piercing tip is configured to pierce tissue.

Example 5

The apparatus of Example 4, wherein at least one barb feature in the plurality of barb features further comprise an inclined face extending from the first piercing tip toward the body.

Example 6

The apparatus of Example 5, wherein at least one barb feature in the plurality of barb features further comprises a vertical face connected to the incline face, wherein the vertical face is configured to anchor the at least one barb feature to pierced tissue.

Example 7

The apparatus of any one or more of Examples 5 through 6, wherein the at least one barb feature of the plurality of barb features further comprises second pair of angled arms and a second piercing tip.

Example 8

The apparatus of Example 7, wherein the first pair of angled arms is connected to the second pair of angled arms by a pair of connecting arms.

Example 9

The apparatus of any one or more of Examples 7 through 8, wherein the first and second angled arms are parallel to each other.

Example 10

The apparatus of any one or more of Examples 1 through 9, wherein the pulling portion is unitarily coupled to the body.

Example 11

The apparatus of any one or more of Examples 1 through 10, wherein the body comprises a plurality of ridges, wherein the locking portion is configured to progressively engage the ridges in response to pulling of the pulling portion relative to the locking portion.

Example 12

The apparatus of Example 11, wherein the locking portion comprises a pawl feature, wherein the pawl feature is configured to ratchet along the ridges in response to pulling of the pulling portion relative to the locking portion.

Example 13

The apparatus of Example 12, wherein the pawl feature and the ridges are configured to enable the pulling portion to travel through the locking portion in a first direction, wherein the pawl feature and the ridges are configured to prevent the pulling portion from traveling through the locking portion in a second direction, wherein the second direction is opposite to the first direction.

Example 14

The apparatus of any one or more of Examples 1 through 13, further comprising a mandrel, wherein the body is configured to wrap around the mandrel.

Example 15

The apparatus of Example 14, wherein the mandrel is configured to fit within a colon, wherein the flexible body is configured to fit around a colon.

Example 16

A method for creating a purse string suture around a colon, wherein the method comprises: (a) wrapping a flexible body around an exterior of the colon, wherein the flexible body includes a plurality of barb features, wherein the barb features extend inwardly toward the colon; (b) cinching the flexible body about the colon to reduce an outer diameter of the colon, thereby creating a cinched region of the colon; (c) piercing the colon with the barb features, thereby anchoring the flexible body to the colon; (d) positioning a circular stapler stapling head assembly in the colon, wherein the stapling head assembly is positioned below the cinched region of the colon; and (e) actuating the stapling head assembly, thereby severing the cinched region of the colon.

Example 17

The method of Example 16, further comprising: (a) advancing a mandrel distally through the colon to an advanced position, wherein the act of wrapping the flexible body around an exterior of the colon is performed at a location corresponding to the advanced position of the mandrel in the colon; and (b) retracting the mandrel proximally through the colon, wherein the act of cinching the flexible body about the colon is performed after the mandrel is retracted proximally through the colon.

Example 18

An apparatus comprising: (a) an anvil collar; (b) a housing comprising: (i) a plurality of staple drivers positioned in a laterally presented and angularly spaced array, (ii) a plurality of staples, wherein each staple of the plurality of staples is positioned adjacent to a corresponding staple driver of the plurality of staple drivers, and (iii) a suture wrapped around the plurality of staples; and (c) mandrel slidably positioned within the housing, wherein the mandrel comprises a laterally presented angled cam surface, wherein the cam surface is configured to actuate the plurality of staple drivers simultaneously to thereby drive the plurality of staples and the suture away outwardly from the housing.

Example 19

The apparatus of Example 18, wherein the mandrel comprises: (i) a head, wherein the annular cam surface is part of the head, and (ii) a drive shaft extending proximally from the head, wherein the drive shaft further extends proximally relative to the housing.

Example 20

The apparatus of Example 18, wherein the anvil collar is configured to deform the plurality of staples in response to the staples being driven outwardly from the housing by the mandrel.

IV. Miscellaneous

It should also be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

At least some of the teachings herein may be readily combined with one or more teachings of U.S. Pat. No. 7,794,475, entitled "Surgical Staples Having Compressible or Crushable Members for Securing Tissue Therein and Stapling Instruments for Deploying the Same," issued Sep. 14, 2010, the disclosure of which is incorporated by reference herein; U.S. Pub. No. 2014/0151429, entitled "Trans-Oral Circular Anvil Introduction System with Dilation Feature," published Jun. 5, 2014, issued as U.S. Pat. No. 9,572,573, on Feb. 21, 2017, the disclosure of which is incorporated by reference herein; U.S. Pub. No. 2014/0144968, entitled "Surgical Staple with Integral Pledget for Tip Deflection," published May 29, 2014, issued as U.S. Pat. No. 9,289,207 on Mar. 22, 2016, the disclosure of which is incorporated by reference herein; U.S. Pub. No. 2014/0158747, now abandoned, entitled "Surgical Stapler with Varying Staple Widths along Different Circumferences," published Jun. 12, 2014, the disclosure of which is incorporated by reference herein; U.S. Pub. No. 2014/0144969, entitled "Pivoting Anvil for Surgical Circular Stapler," published May 29, 2014, issued as U.S. Pat. No. 9,498,222 on Nov. 22, 2016, the disclosure of which is incorporated by reference herein; U.S. Pub. No. 2014/0151430, entitled "Circular Anvil Introduction System with Alignment Feature," published Jun. 5, 2014, issued as U.S. Pat. No. 9,724,100 on Aug. 8, 2017, the disclosure of which is incorporated by reference herein; U.S. Pub. No. 2014/0166717, entitled "Circular Stapler with Selectable Motorized and Manual Control, Including a Control Ring," published Jun. 19, 2014, issued as U.S. Pat. No. 9,532,783 on Jan. 3, 2017, the disclosure of which is incorporated by reference herein; U.S. Pub. No. 2014/0166728, entitled "Motor Driven Rotary Input Circular Stapler with Modular End Effector," published Jun. 19, 2014, issued as U.S. Pat. No. 9,597,081 on Mar. 21, 2017, the disclosure of which is incorporated by reference herein; and/or U.S. Pub. No. 2014/0166718, entitled "Motor Driven Rotary Input Circular Stapler with Lockable Flexible Shaft," published Jun. 19, 2014, issued as U.S. Pat. No. 9,463,022 on Oct. 11, 2016, the disclosure of which is incorporated by reference herein. Various suitable ways in which such teachings may be combined will be apparent to those of ordinary skill in the art.

While the examples herein have been provided in the context of a circular stapling instrument, it should be understood that the various teachings herein may be readily applied to various other kinds of surgical instruments. By way of example only, the various teachings herein may be readily applied to linear stapling devices (e.g., endocutters). For instance, various teachings herein may be readily combined with various teachings of U.S. Pub. No. 2012/0239012, entitled "Motor-Driven Surgical Cutting Instrument with Electric Actuator Directional Control Assembly," published Sep. 20, 2012, issued as U.S. Pat. No. 8,463,022 on Jun. 4, 2013, the disclosure of which is incorporated by reference herein, and/or U.S. Pub. No. 2010/0264193, entitled "Surgical Stapling Instrument with An Articulatable End Effector," published Oct. 21, 2010, issued as U.S. Pat. No. 8,408,439 on Apr. 2, 2013, the disclosure of which is incorporated by reference herein, as will be apparent to those of ordinary skill in the art. As another merely illustrative example, the various teachings herein may be readily applied to a motorized electrosurgical device. For instance, various teachings herein may be readily combined with various teachings of U.S. Pub. No. 2012/0116379, entitled "Motor Driven Electrosurgical Device with Mechanical and Electrical Feedback," published May 10, 2012, issued as U.S. Pat. No. 9,161,803 on Oct. 20, 2015, the disclosure of which is incorporated by reference herein, as will be apparent to those of ordinary skill in the art. Other suitable kinds of instruments in which the teachings herein may be applied, and various ways in which the teachings herein may be applied to such instruments, will be apparent to those of ordinary skill in the art.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus comprising:
   (a) a locking portion;
   (b) a flexible pulling portion, wherein the locking portion is configured to receive the pulling portion, wherein the pulling portion is configured to engage and translate relative to the locking portion after the locking portion has received the pulling portion;
   (c) a flexible body, wherein the flexible body extends from the locking portion to the pulling portion, wherein the flexible body is configured to form a loop when the pulling portion engages the locking portion, wherein the loop is configured to decrease in size in response to pulling of the pulling portion relative to the locking portion; and
   (d) a plurality of barb features extending laterally from the body, wherein the barb features are configured to engage a tubular region of tissue and thereby form pleats in the tubular region of tissue, wherein each barb feature in the plurality of barb features defines a retaining gap, wherein the flexible pulling portion is slidably coupled within the retaining gap of each barb feature of the plurality of barb features such that the flexible pulling portion is slidable relative to the barb features, wherein each barb feature in the plurality of barb features comprises a base, a pair of upper angled arms extending from the base and terminating into a first point, and a pair of lower angled arms extending from the base and terminating into a second point.

2. The apparatus of claim 1, wherein the locking portion is configured to restrict translation of the pulling portion to a single direction.

3. The apparatus of claim 1, wherein the first point of each barb feature in the plurality of barb feature comprises a first piercing tip, wherein the first piercing tip is configured to pierce tissue.

4. The apparatus of claim 3, wherein each barb feature in the plurality of barb features further comprise an inclined face extending from the first piercing tip toward the body.

5. The apparatus of claim 4, wherein each barb feature in the plurality of barb features further comprises a vertical face connected to the incline face, wherein the vertical face is configured to anchor the barb feature to pierced tissue.

6. The apparatus of claim 4, wherein the second point of said each barb feature comprises a second piercing tip.

7. The apparatus of claim 6, wherein the first pair of angled arms is connected to the second pair of angled arms by a pair of connecting arms in said each barb feature.

8. The apparatus of claim 6, wherein the first pair of angled arms and the second pair of angled arms are parallel to each other in said each barb feature.

9. The apparatus of claim 1, wherein the body comprises a plurality of ridges, wherein the locking portion is configured to progressively engage the ridges in response to pulling of the pulling portion relative to the locking portion.

10. The apparatus of claim 9, wherein the locking portion comprises a pawl feature, wherein the pawl feature is configured to ratchet along the ridges in response to pulling of the pulling portion relative to the locking portion.

11. The apparatus of claim 10, wherein the pawl feature and the ridges are configured to enable the pulling portion to travel through the locking portion in a first direction, wherein the pawl feature and the ridges are configured to prevent the pulling portion from traveling through the locking portion in a second direction, wherein the second direction is opposite to the first direction.

12. The apparatus of claim 1, further comprising a mandrel, wherein the body is configured to wrap around the mandrel.

13. The apparatus of claim 12, wherein the mandrel is configured to fit within a colon, wherein the flexible body is configured to fit around a colon.

14. An apparatus comprising:
(a) a locking portion;
(b) a flexible pulling portion, wherein the locking portion is configured to receive the pulling portion, wherein the pulling portion is configured to engage and translate relative to the locking portion after the locking portion has received the pulling portion to define a loop; and
(c) a plurality of barb features, wherein the barb features are configured to engage a tubular region of tissue and thereby form pleats in the tubular region of tissue, wherein each barb feature in the plurality of barb features defines a retaining gap, wherein the flexible pulling portion is slidably disposed within the retaining gap of each barb feature such that the flexible pulling portion is slidable in the retaining gap of each barb feature, wherein each barb feature in the plurality of barb features comprises a base, a pair of upper angled arms extending from the base and terminating into a first point, and a pair of lower angled arms extending from the base and terminating into a second point.

15. The apparatus of claim 14, further comprising a first retainer extending from the pair of upper angled arms in said each barb feature and a second retainer extending from the pair of lower angled arms in said each barb feature, wherein the first retainer and the second retainer partially define the retaining gap of said each barb feature.

16. The apparatus of claim 14, further comprising a flexible body connecting the plurality of barb features.

17. An apparatus comprising:
(a) a locking portion;
(b) a flexible pulling portion, wherein the locking portion is configured to receive the pulling portion, wherein the pulling portion is configured to engage and translate relative to the locking portion after the locking portion has received the pulling portion;
(c) a flexible body, wherein the flexible body extends from the locking portion to the pulling portion, wherein the flexible body is configured to form a loop when the pulling portion engages the locking portion, wherein the loop is configured to decrease in size in response to pulling of the pulling portion relative to the locking portion; and
(d) a plurality of barb features extending laterally from the body, wherein the barb features are configured to engage a tubular region of tissue and thereby form pleats in the tubular region of tissue, wherein each barb feature in the plurality of barb features defines a gap, wherein the flexible pulling portion is slidably disposed in the gap of each barb feature in the plurality of barb features such that the flexible pulling portion is slidable in the gap of each barb feature, wherein each barb feature in the plurality of barb features comprises a base, a pair of upper angled arms extending from the base and terminating into a first point, and a pair of lower angled arms extending from the base and terminating into a second point.

* * * * *